(12) United States Patent
Taneda et al.

(10) Patent No.: US 10,564,038 B2
(45) Date of Patent: Feb. 18, 2020

(54) SPECTRAL CHARACTERISTIC ACQUIRING APPARATUS, IMAGE FORMING APPARATUS, IMAGE FORMING SYSTEM, IMAGE FORMING APPARATUS MANAGEMENT SYSTEM, AND IMAGE FORMING APPARATUS MANAGEMENT METHOD

(71) Applicants: Yusuke Taneda, Kanagawa (JP); Kohei Shimbo, Kanagawa (JP); Yoichi Kubota, Tokyo (JP)

(72) Inventors: Yusuke Taneda, Kanagawa (JP); Kohei Shimbo, Kanagawa (JP); Yoichi Kubota, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/253,875

(22) Filed: Jan. 22, 2019

(65) Prior Publication Data

US 2019/0250040 A1    Aug. 15, 2019

(30) Foreign Application Priority Data

Feb. 15, 2018    (JP) .................................. 2018-025231

(51) Int. Cl.
*G01J 3/46*    (2006.01)
*G01J 3/52*    (2006.01)
(Continued)

(52) U.S. Cl.
CPC ............. *G01J 3/524* (2013.01); *G01J 3/2823* (2013.01); *H04N 1/0057* (2013.01); *H04N 1/6027* (2013.01)

(58) Field of Classification Search
CPC ........ G01J 3/46; G01J 3/50; G01J 3/02; G01J 3/524; G01J 3/51
(Continued)

(56) References Cited

U.S. PATENT DOCUMENTS 7,973,928 B2   7/2011   Iwane
8,363,217 B2   1/2013   Seo et al.
(Continued)

FOREIGN PATENT DOCUMENTS

EP    0177461    4/1986
EP    0831639    3/1998
(Continued)

OTHER PUBLICATIONS

Extended European Search Report for 19153927.9 dated Jul. 22, 2019.

*Primary Examiner* — Md M Rahman
(74) *Attorney, Agent, or Firm* — IPUSA, PLLC

(57) ABSTRACT

A spectral characteristic acquiring apparatus includes a color data acquiring unit including a plurality of spectral sensors configured to receive reflected light from an object that has been irradiated with light to acquire color data of the object, a spectral characteristic calculating unit configured to estimate spectral characteristics of the object based on the acquired color data of the object using a preset transformation matrix, a first conveying unit configured to convey the object in a predetermined conveying direction, and a second conveying unit configured to convey the color data acquiring unit in a direction intersecting the predetermined conveying direction. The plurality of spectral sensors are arrayed in the predetermined conveying direction.

10 Claims, 17 Drawing Sheets

(51) Int. Cl.
*H04N 1/00* (2006.01)
*H04N 1/60* (2006.01)
*G01J 3/28* (2006.01)

(58) Field of Classification Search
USPC ........................................................ 356/402
See application file for complete search history.

(56) References Cited

U.S. PATENT DOCUMENTS

| | | | |
|---|---|---|---|
| 8,472,019 | B2 | 6/2013 | Seo et al. |
| 8,497,988 | B2 | 7/2013 | Shimbo et al. |
| 8,559,005 | B2 | 10/2013 | Shimbo et al. |
| 8,593,628 | B2 | 11/2013 | Shimbo et al. |
| 8,755,046 | B2 | 6/2014 | Shimbo et al. |
| 8,879,057 | B2 | 11/2014 | Shimbo et al. |
| 8,908,176 | B2 | 12/2014 | Kubota et al. |
| 8,964,176 | B2 | 2/2015 | Kamijo et al. |
| 9,068,893 | B2 | 6/2015 | Seo et al. |
| 9,197,761 | B2 | 11/2015 | Kamijo et al. |
| 9,222,833 | B2 | 12/2015 | Seo et al. |
| 9,224,080 | B2 | 12/2015 | Kubota et al. |
| 9,677,938 | B2 | 6/2017 | Shimbo et al. |
| 10,015,367 | B2 | 7/2018 | Urushidani |
| 2007/0230657 | A1* | 10/2007 | Garms ................ G01N 23/046 378/57 |
| 2013/0182256 | A1* | 7/2013 | Kubota .................... G01J 3/42 356/402 |
| 2015/0350493 | A1 | 12/2015 | Sakatani |

FOREIGN PATENT DOCUMENTS

| | | |
|---|---|---|
| EP | 2839966 | 2/2015 |
| EP | 2916116 | 9/2015 |
| JP | 2003-014546 | 1/2003 |
| JP | 2011-013201 | 1/2011 |
| JP | 4985061 | 7/2012 |
| JP | 5880053 | 3/2016 |
| JP | 2017-053805 | 3/2017 |

* cited by examiner

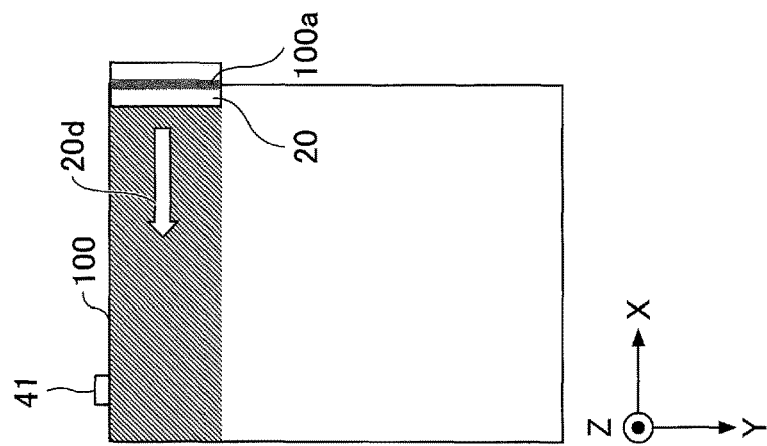
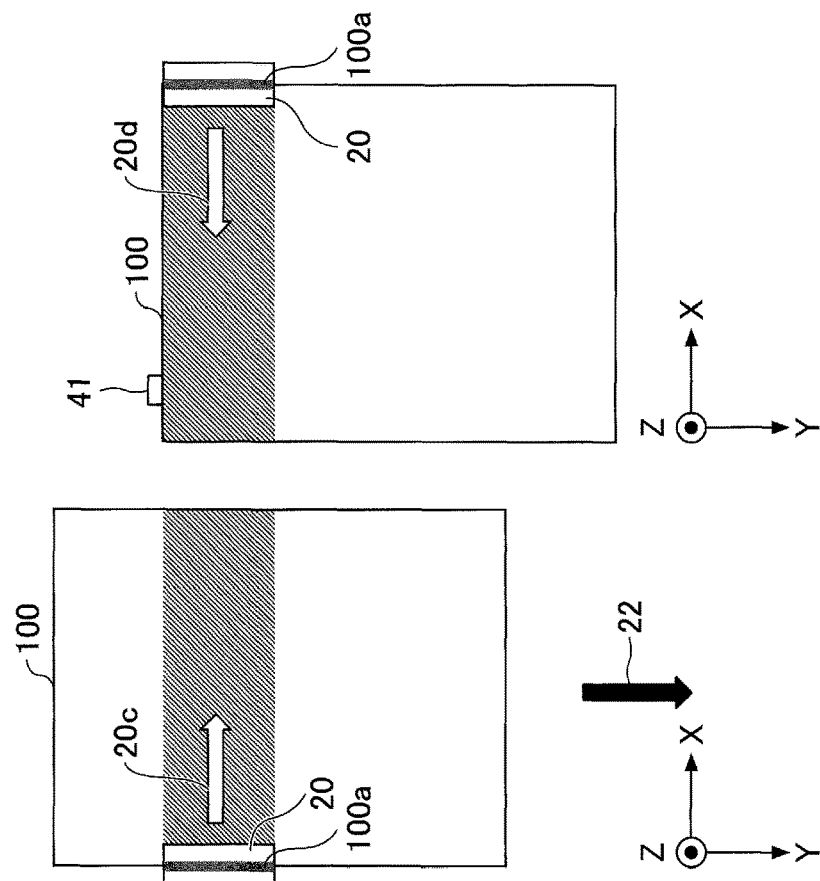
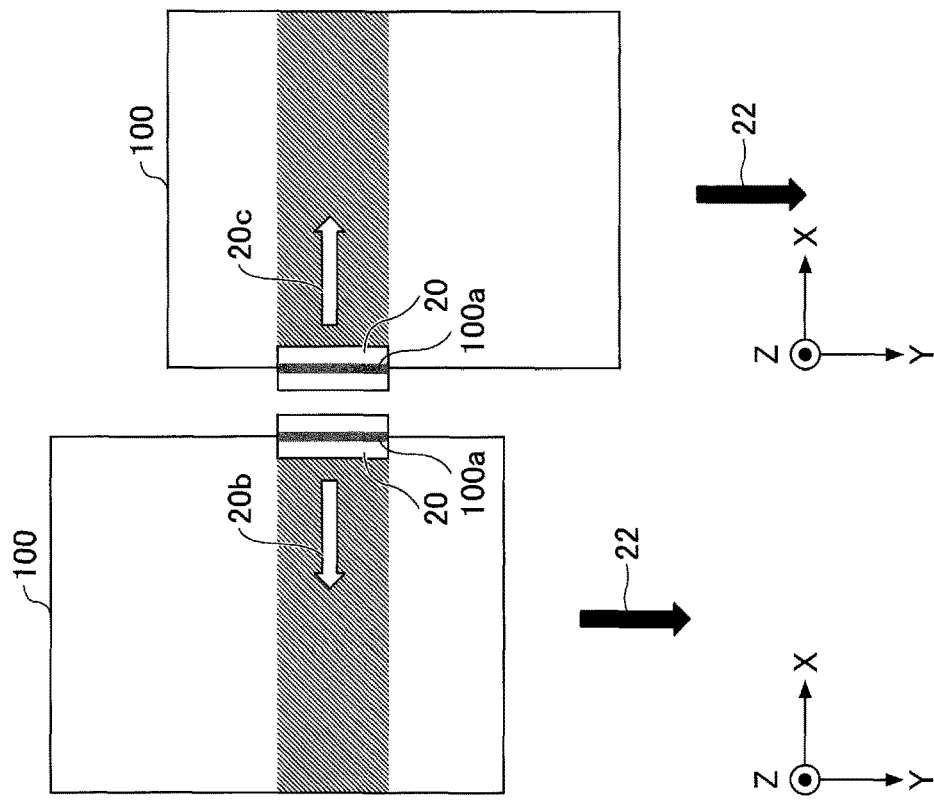
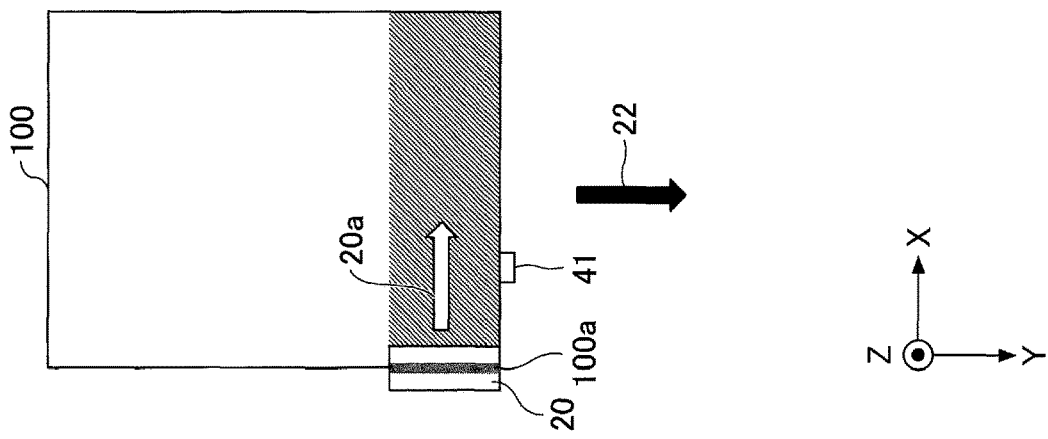

FIG.12

| COLOR TARGET \ SPECTRAL SENSOR | $80_1$ | $80_2$ | $80_3$ | ... |
|---|---|---|---|---|
| A | L*a*b*... | L*a*b*... | L*a*b*... | ... |
| B | L*a*b*... | L*a*b*... | L*a*b*... | ... |
| C | L*a*b*... | L*a*b*... | L*a*b*... | ... |
| ... | ... | ... | ... | ... |

SPECTRAL CHARACTERISTIC ACQUIRING APPARATUS, IMAGE FORMING APPARATUS, IMAGE FORMING SYSTEM, IMAGE FORMING APPARATUS MANAGEMENT SYSTEM, AND IMAGE FORMING APPARATUS MANAGEMENT METHOD

CROSS-REFERENCE TO RELATED APPLICATIONS

The present application claims priority under 35 U.S.C. § 119 to Japanese Patent Application No. 2018-025231 filed on Feb. 15, 2018, the entire contents of which are incorporated herein by reference.

BACKGROUND OF THE INVENTION

1. Field of the Invention

The present invention relates to a spectral characteristic acquiring apparatus, an image forming apparatus, an image forming system, an image forming apparatus management system, and an image forming apparatus management method.

2. Description of the Related Art

In recent years, high image quality is demanded in color images formed on recording media such as paper by full-color image forming apparatuses (printers, copiers, etc.) adopting the electrophotographic method, the inkjet method, and the like, and improvement of color reproducibility is one of the important technical challenges in the field.

In order to improve color reproducibility, a technique is known for acquiring spectral characteristics of an image formed on a recording medium based on output signals obtained from a plurality of spectral sensors arranged in a direction orthogonal to the conveying direction of the recording medium (see, e.g., Japanese Patent No. 5880053). Also, a scanning colorimetric technique is known for two-dimensionally scanning a measurement object such as a color patch using a spectral sensor to measure the color of the measurement object (see, e.g., Japanese Unexamined Patent Publication No. 2003-014546).

However, according to the technique described in Japanese Patent No. 5880053, a linear bright light source that is capable of illuminating a wide range is required in order to accurately acquire spectral characteristics across the width of an image, and as such, an apparatus employing such technique may be rather expensive. Also, according to the technique described in Japanese Unexamined Patent Publication No. 2003-014546, the spectral sensor is used to perform two-dimensional scanning, and as such, it takes time to acquire spectral characteristics of a measurement object. Because spectral characteristics of color patches of 5000 to 10000 colors have to be acquired, it is impractical to apply this technique to an image of a multicolor printer using six or more colors, for example.

SUMMARY OF THE INVENTION

An aspect of the present invention is directed to providing a low-cost spectral characteristic acquiring apparatus that uses a plurality of arrayed spectral sensors.

According to one embodiment of the present invention, a spectral characteristic acquiring apparatus is provided that includes a color data acquiring unit including a plurality of spectral sensors configured to receive reflected light from an object that has been irradiated with light to acquire color data of the object, a spectral characteristic calculating unit configured to estimate spectral characteristics of the object based on the acquired color data of the object using a preset transformation matrix, a first conveying unit configured to convey the object in a predetermined conveying direction, and a second conveying unit configured to convey the color data acquiring unit in a direction intersecting the predetermined conveying direction. The plurality of spectral sensors are arrayed in the predetermined conveying direction.

BRIEF DESCRIPTION OF THE DRAWINGS

FIGS. 7A-7D are plan views of a sheet viewed from the +Z axis direction while color data acquisition is performed by the spectral characteristic acquiring apparatus according to the first embodiment;

FIG. 12 is a diagram illustrating example spectral characteristics acquired for each color target by each spectral sensor of the spectral characteristic acquiring apparatus according to the first embodiment;

DESCRIPTION OF THE EMBODIMENTS

Figure 1:
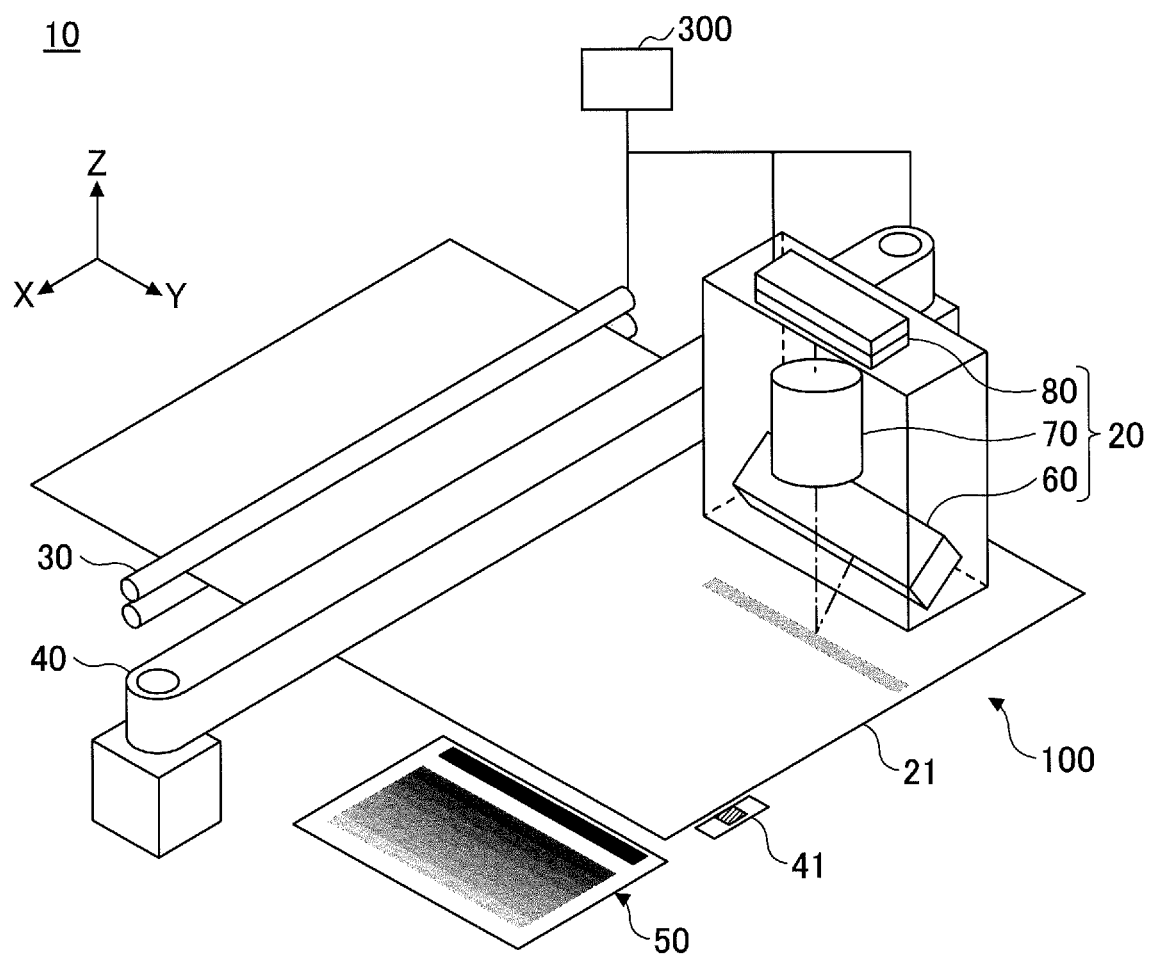
FIG. 1 is a perspective view diagram illustrating an example configuration of a spectral characteristic acquiring apparatus according to a first embodiment of the present invention.

In the following, embodiments of the present invention will be described with reference to the accompanying drawings. Note that in the drawings, elements having substantially the same features or configurations are given the same reference numerals and overlapping descriptions thereof may be omitted.

Note that in the present description of embodiments, an image carrying medium such as paper is illustrated as an example of an object of spectral characteristic acquisition, and such an object of spectral characteristic acquisition is simply referred to as "paper". Also, note that solid arrows indicating X-axis, Y-axis, and Z-axis directions in the drawings respectively represent the width direction of the paper, the paper conveying direction, and a direction orthogonal to the X-Y plane. The X-axis direction is an example of "a direction intersecting a predetermined conveying direction", and the Y-axis direction is an example of "a predetermined conveying direction".

Also, in the present description of embodiments, the terms "image formation", "recording", "printing", "shaping", and the like are all used synonymously.

First Embodiment

In the following, a first embodiment of the present invention will be described with reference to the drawings. FIG. 1 is a perspective view diagram illustrating an example configuration of a spectral characteristic acquiring apparatus according to the present embodiment.

In FIG. 1, the spectral characteristic acquiring apparatus 10 includes a color data acquiring unit 20, a paper conveying unit 30, a paper detection sensor 41, a color data acquiring unit conveying unit 40, a calibration color target 50, and a control unit 300. Further, the color data acquiring unit 20 includes a line illuminating light source 60, a reducing imaging lens 70, and a spectroscopic unit 80. The color data acquiring unit 20 is an example of a color data acquiring unit. Further, the paper conveying unit 30 is an example of a "first conveying unit", and the color data acquiring unit conveying unit 40 is an example of a "second conveying unit".

A sheet of paper 100 is conveyed in the Y-axis direction at a constant speed by the paper conveying unit 30. The paper conveying unit 30 may be configured by a nip roller having two rollers, for example. The paper conveying unit 30 conveys the paper 100 by nipping the paper 100 with a nip roller and rotating the nip roller.

The paper detection sensor 41 detects that the paper 100 has been conveyed to the position of a color data acquiring region 21. For example, the paper detection sensor 41 may irradiate the paper 100 with light and detect reflected light reflected by the paper 100 with a photodiode or the like. Based on the output of the paper detection sensor 41, a determination may be made that the paper 100 is located at the position of the color data acquiring region 21 from which the color data acquiring unit 20 acquires color data.

The color data acquiring unit conveying unit 40 conveys the color data acquiring unit 20 in the paper width direction. The color data acquiring unit conveying unit 40 may be a conveying stage including a ball screw and a guide, for example.

The calibration color target 50 is used when calibrating a transformation matrix that is used for calculating spectral characteristics. Note that the calibration color target 50 will be described in detail below.

The spectral characteristic acquiring apparatus 10 can simultaneously acquire the spectral characteristics of a plurality of positions in the Y-axis direction within the color data acquiring region 21 of the paper 100.

The line illuminating light source 60 illuminates the color data acquiring region 21 with linear light from a direction that is approximately 45 degrees with respect to the normal direction of the paper 100. Also, the line illuminating light source 60 illuminates an appropriate region with respect to the color data acquiring region 21 so that reflected light from a region of the paper 100 other than that at the color data acquiring region 21 does not enter the spectroscopic unit 80.

The line illuminating light source 60 may be configured by a white LED (Light Emitting Diode) array having intensity across substantially the entire visible light region, for example. However, the present invention is not limited thereto, and a fluorescent lamp such as a cold cathode fluorescent lamp or a lamp light source may also be used as the line illuminating light source 60.

The line illuminating light source 60 is preferably a light source that emits light in a wavelength region required for spectroscopy and is capable of uniformly illuminating the entire color data acquiring region 21. Note that in some embodiments, a collimating lens for converging light emitted from the line illuminating light source 60 and irradiating the paper 100 with parallel light or convergent light may be added.

The reducing imaging lens 70 is arranged so that its optical axis coincides with the normal direction of the paper 100 and has a function of imaging reflected light (i.e., reflected light beam) from the paper 100 on a plane of incidence of the spectroscopic unit 80 at a predetermined magnification. Note that by adding image-side telecentricity to the reducing imaging lens 70, the chief ray of the light beam incident on an image plane becomes substantially parallel to the optical axis. The reducing imaging lens 70 may be composed of a plurality of lenses.

Note that by adding image-side telecentricity to the reducing imaging lens 70, the chief ray of the light beam incident on the image plane may be easily made substantially parallel to the optical axis. However, the reducing imaging lens 70 does not have to be provided with image-side telecentricity. In such case, an effect similar to that described above may be obtained by adjusting the positional relationship between each pinhole of a pinhole array and each lens of a lens array in accordance with the inclination of the chief ray at each position on the image plane as described below.

The spectroscopic unit 80 has a function of spectrally diffusing and reflecting light irradiated on the paper 100 and a function of outputting a signal receiving the dispersed light. Note that the spectroscopic unit 80 will be described in detail below with reference to FIG. 2.

Note that the optical system illustrated in FIG. 1 is a so-called 45/0 optical system in which the illuminating light emitted from the line illuminating light source 60 is obliquely incident on the paper 100 at approximately 45 degrees with respect to the paper 100, and the spectroscopic unit 80 receives diffused light scattered from the paper 100 in the vertical direction by diffuse reflection. However, the configuration of the optical system is not limited to the example illustrated in FIG. 1. For example, a so-called 0/45 optical system may be used in which illuminating light emitted from the line illuminating light source 60 is vertically incident on the paper 100, and the spectroscopic unit 80 receives diffused light scattered from the paper 100 at 45 degrees.

Figure 2:
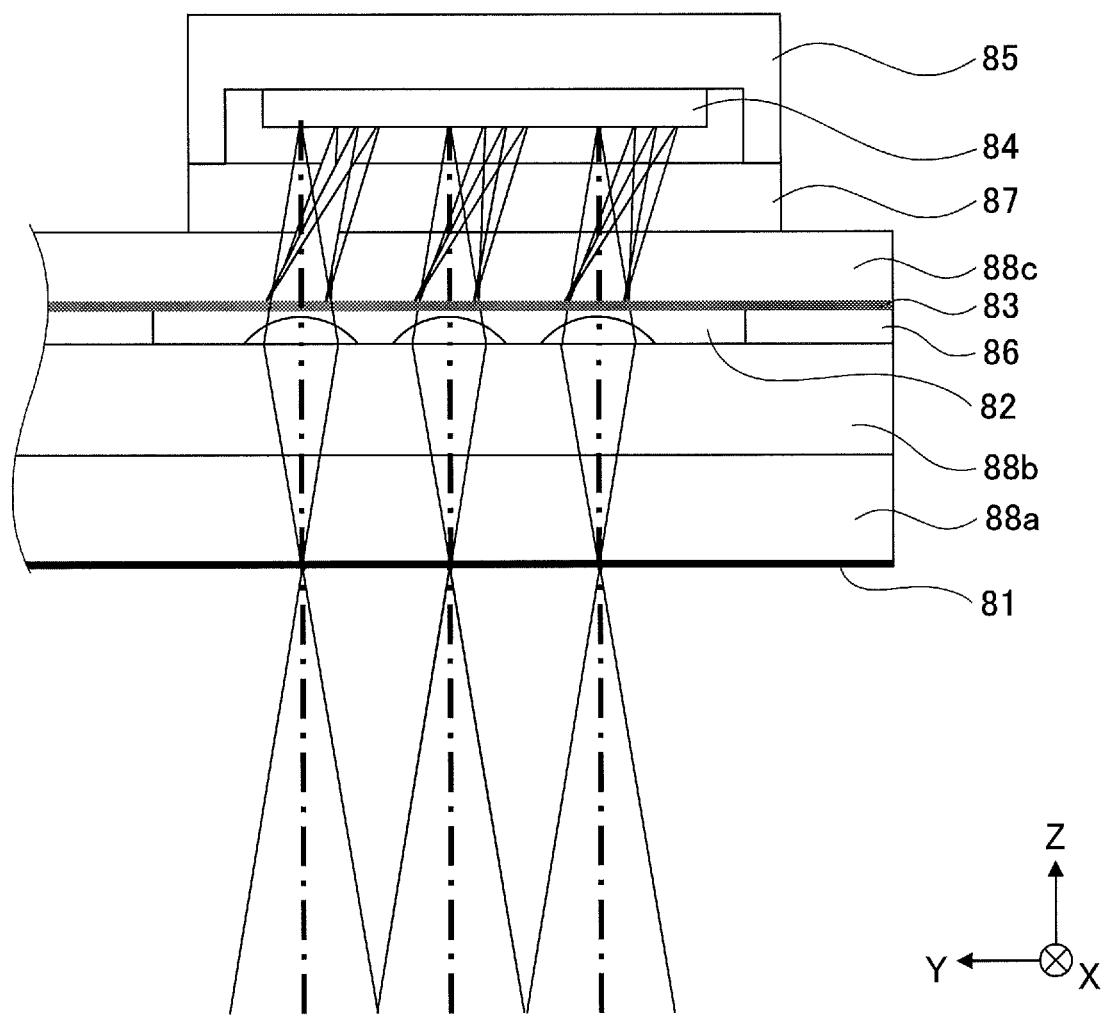
FIG. 2 is a diagram illustrating an example configuration of a spectroscopic unit of the spectral characteristic acquiring apparatus according to the first embodiment.

In the following, the configuration of the spectroscopic unit 80 will be described with reference to FIG. 2. FIG. 2 is an example cross-sectional view of the spectroscopic unit 80 according to the first embodiment. Specifically, FIG. 2 illustrates a partial cross section of the spectroscopic unit 80 that is parallel to the YZ plane of the spectroscopic unit 80.

In FIG. 2, the spectroscopic unit 80 includes a pinhole array 81, a lens array 82, a diffraction element 83, and an imaging element 84. Further, the spectroscopic unit 80 includes a package 85, a spacer 86, a cover glass 87, and glass base materials 88a to 88c.

The pinhole array 81 has pinholes as openings through which reflected light from the paper 100 passes. The pinholes are arranged at an image plane position in the Z-axis direction corresponding to where light incident from the reducing imaging lens 70 forms an image and are arranged at predetermined intervals in the Y-axis direction to form an array. FIG. 2 illustrates an example in which three pinholes are arranged in the Y-axis direction.

The pinhole array 81 is integrally arranged on the glass base material 88a, which is a transparent flat glass plate provided as a light-transmissive frame. For example, the pinhole array 81 may be configured by a metal thin film made of nickel or the like deposited on the transparent glass base material and having openings corresponding to pinholes arranged into an array. The light beams of reflected light from respective positions of the color data acquiring region 21 of the paper 100 are extracted by the pinholes arranged in the pinhole array 81.

Note that the configuration of the spectroscopic unit 80 is not limited to that using the pinhole array 81. For example, a slit array having rectangular openings or an oblique slit array having rectangular slits inclined with respect to the Y-axis direction may also be used.

The glass base material 88b, which is a transparent flat glass plate provided as a light-transmissive frame, is bonded face-to-face with the surface of the glass base material 88a on the opposite side of the surface on which reflected light from the paper 100 is incident. The surface of the glass base material 88b on the opposite side of the bonding surface with the glass base material 88a has lenses arranged into an array at predetermined intervals in the Y-axis direction. FIG. 2 illustrates an example in which three lenses are arranged in the Y-axis direction to form the lens array 82. Each lens of the lens array 82 focuses a light beam that has passed through a pinhole of the pinhole array 81, and an image by each lens is formed on the imaging element 84.

The lens array 82 has a plurality of lenses 82a arranged into one line extending in the Y-axis direction, and each lens 82a of the lens array 82 has the function of converting a diffused light beam that has passed through an opening of the pinhole array 81 into a weakly diffused light beam.

Note that a weakly diffused light beam refers to a diffused light beam that is closer to a parallel light beam than the incident diffused light beam. That is, a weakly diffused light beam refers to a diffused light beam whose degree of diffusion has been reduced, i.e., weakened, as compared with the incident diffused light beam.

Each lens 82a of the lens array 82 is arranged at a position corresponding to an opening (pinhole) of the pinhole array 81. The diameter of each lens 82a is arranged so that all the light transmitted through its corresponding opening would be incident thereon. Note, however, that the planar shape of each lens 82a does not have to be circular.

In the present embodiment, the glass base materials 88a and 88b are arranged between the pinhole array 81 and the lens array 82. However, the present invention is not limited thereto. The thicknesses of the glass base materials 88a and 88b are determined such that the optical path lengths of the pinhole array 81 and the lens array 82 are shorter than the object-side focal length of each lens 82a of the lens array 82. Note that portions of the lens array 82 other than the openings of the lenses 82a are preferably shielded in order to eliminate stray light.

The glass base material 88c, which is a transparent flat glass plate provided as a light-transmissive frame is arranged to face the lens array 82 in the Z-axis direction. The glass base material 88b and the glass base material 88c are bonded to each other via a spacer 86.

The spacer 86 is a member for providing a predetermined space, i.e., a space between the glass base material 88b and the glass base material 88c. For example, the spacer 86 may be a metal flat plate having a predetermined through hole formed in its flat portion. A portion of the spacer 86 that is facing the lens array 82 and does not correspond to the through hole and a portion of the glass base material 88 that does not have a lens formed thereon come into contact with each other and are bonded. Also, a portion of the spacer 86 that is facing the diffraction element 83 and does not correspond to the through hole and a portion of the glass base material 88b that does not have a lens formed there on come into contact with each other and are bonded. In this way, a predetermined gap (i.e., a space) is provided between the glass base material 88b and the glass base material 88c. Note that the through hole of the spacer 86 may be a small hole for accommodating each lens of the lens array 82 or a large hole for accommodating a plurality of lenses of the lens array 82, for example.

The diffraction element 83 is arranged on the surface of the glass base material 88c facing the lens array 82, i.e., the surface on which the reflected light from the paper 100 is incident. The diffraction element 83 has sawtooth-shaped structures formed at predetermined intervals on the glass base material 88c, and functions as a diffraction grating that diffracts and disperses incident light. The light beams transmitted through the respective lenses of the lens array 82 are dispersed by the diffraction element 83. Diffraction images corresponding to the light beams are formed on the imaging element 84.

The diffraction element 83 is preferably a blazed diffraction grating with enhanced diffraction efficiency in the first diffraction order. By using a blazed diffraction grating as the diffraction element 83, only the diffraction efficiency in the first diffraction order can be enhanced, and in this way, the light utilization efficiency of the optical system can be enhanced. As a result, signals of sufficient quality can be acquired in a short time, and the time for acquiring spectral characteristics can be shortened.

The imaging element 84 is a line sensor having a plurality of pixels arranged in the Y-axis direction. The imaging element 84 acquires the quantity of incident light of a predetermined wavelength band by having a plurality of light receiving elements arranged at different positions receive the respective diffraction images formed by the lens array 82 and the diffraction element 83. The imaging element 84 may be, for example, a MOS (Metal Oxide Semiconductor Device), a CMOS (Complementary Metal Oxide Semiconductor Device), a CCD (Charge Coupled Device), or the like.

Figure 3:
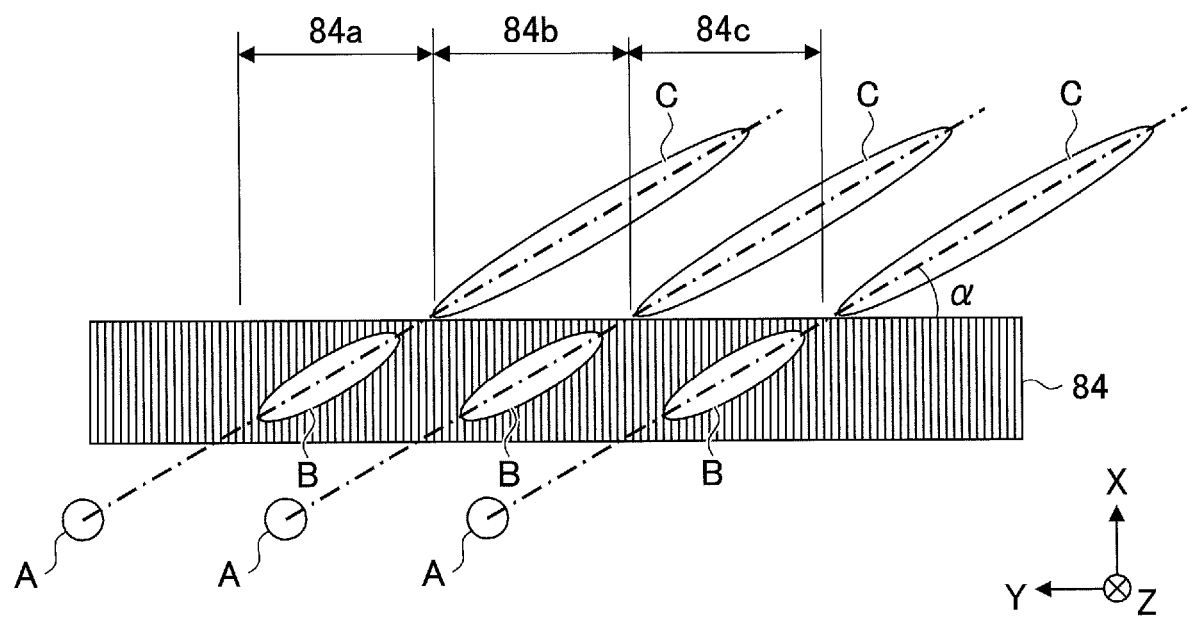
FIG. 3 is a diagram illustrating diffraction images being received by an imaging element of the spectral characteristic acquiring apparatus according to the first embodiment.

The diffraction axis of the diffraction element 83 is inclined at an angle α with respect to the Y-axis direction. As can be appreciated from FIG. 3, diffraction images inclined at the angle α with respect to the X-axis direction are incident on the imaging element 84. In FIG. 3, three diffraction patterns each consisting of a zero order diffraction image A, a first order diffraction image B, and a second order diffraction image C are arranged side by side in the Y-axis direction. The imaging element 84 is configured to receive the first order diffraction image B of each diffraction pattern. In FIG. 3, three primary diffraction images of three lens arrays are received at pixel regions 84a, 84b, and 84c of the imaging element 84 and converted into electric signals. The electric signals are output as color data acquired by the spectroscopic unit 80.

As described above, in the spectral characteristic acquiring apparatus 10, crosstalk of the diffraction images can be eliminated, and the spectral characteristic of the paper 100 can be obtained from the first order diffraction image B. In the following description, the first order diffraction image B may be simply referred to as a "diffraction image".

The imaging element 84 is fixed inside the package 85, and an opening of the package 85 is closed with a transparent cover glass 87 that is provided as a light-transmissive frame. The cover glass 87 is bonded to the surface of the glass base material 88c on the opposite side of the surface on which the diffraction element 83 is formed.

Note that optically speaking, one pinhole of the pinhole array 81, one lens of the lens array 82 corresponding thereto, a part of the diffraction element 83, i.e., a part transmitting the light beam from the lens, and a part of the pixel array of the imaging element 84 implement the function of one spectrometer. As such, in the following description, a part of the spectroscopic unit 80 implementing the function of one spectroscope may be referred to as a spectral sensor.

Note that although only three spectral sensors are illustrated in FIGS. 2 and 3, the number of spectral sensors is not particularly limited, and the spectroscopic unit 80 may be configured to have a large number of spectral sensors. For example, if a 1024-pixel image sensor is used as the imaging element 84 and the number of pixels included in the above-described part of the pixel array of the imaging element 84 is 10 pixels, 102 spectral sensors may be provided. The spectral sensors may be arrayed in the Y-axis direction, i.e., the paper conveying direction, and are examples of "plurality of spectral sensors arrayed in the predetermined conveying direction".

In the optical system including the spectroscopic unit 80, relative positional deviations between the imaging element 84 and the diffraction images formed by the pinhole array 81, the lens array 82, and the diffraction element 83 substantially influence the spectral characteristic acquisition accuracy. In the present embodiment, the pinhole array 81, the lens array 82, the diffraction element 83, and the imaging element 84 are stacked in the direction of the optical axis of the reducing imaging lens 70 and bonded together to form an integrated unit.

Figure 4:
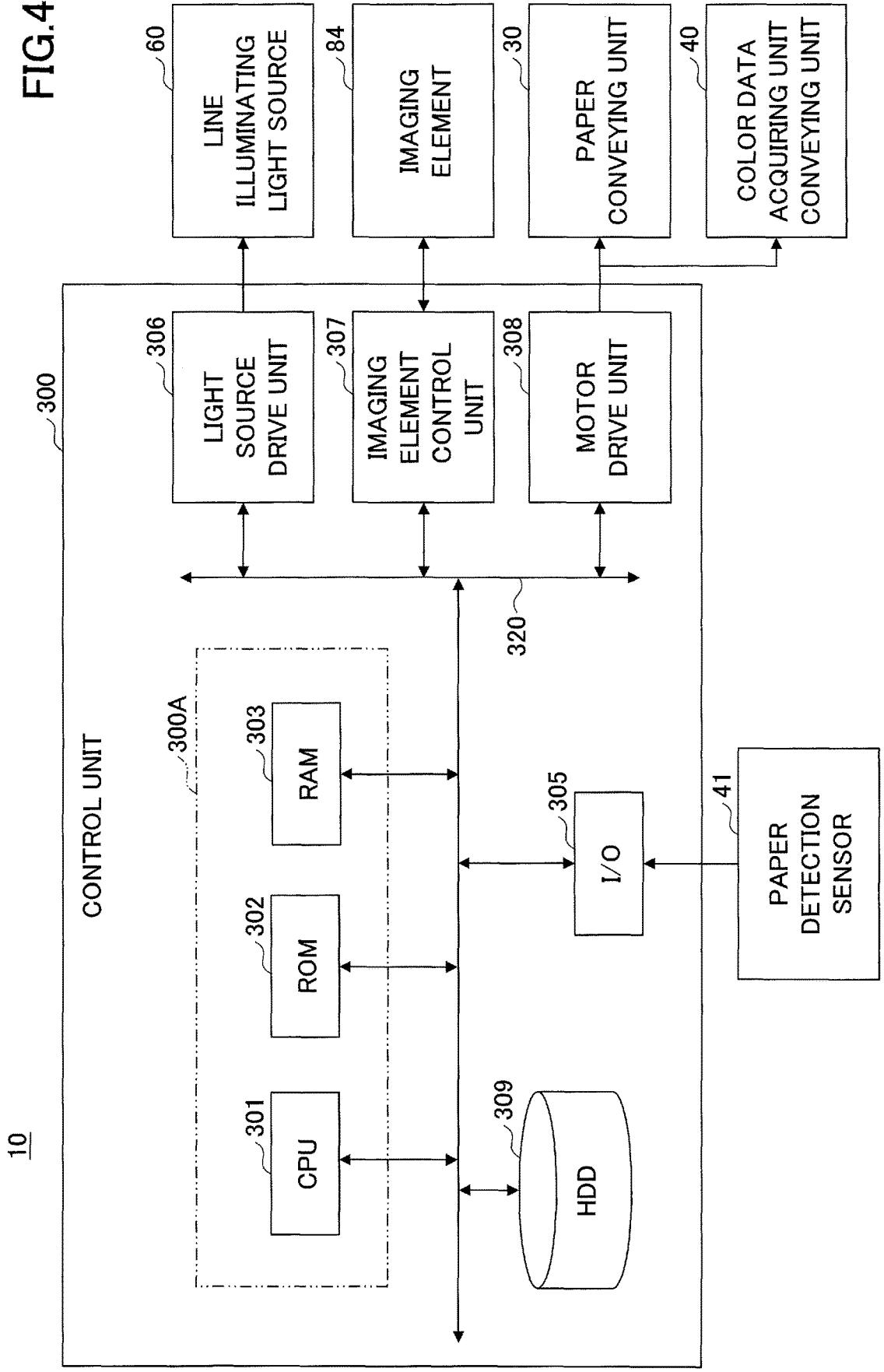
FIG. 4 is a block diagram illustrating an example hardware configuration of the spectral characteristic acquiring apparatus according to the first embodiment.

In the following, the control unit 300 of the spectral characteristic acquiring apparatus 10 will be described with reference to FIG. 4. FIG. 4 is a block diagram illustrating an example hardware configuration of the spectral characteristic acquiring apparatus 10 according to the present embodiment.

The control unit 300 includes a main control unit 300A, an I/O (input/output) 305, a light source drive unit 306, an imaging element control unit 307, a motor drive unit 308, and a HDD (hard disk drive) 309.

The main control unit 300A includes a CPU (central processing unit) 301, a ROM (read only memory) 302, and a RAM (random access memory) 303. The above elements are electrically connected to each other via a system bus 320.

The CPU 301 comprehensively controls the operation of the spectral characteristic acquiring apparatus 10. The CPU 301 uses the RAM 303 as a work area to execute a program stored in the ROM 302 to thereby control the overall operation of the spectral characteristic acquiring apparatus 10 and implement various functions as described below. The HDD 309 stores acquired color data and the like.

The I/O 305 inputs a signal detected by the paper detection sensor 41 and the like.

The light source drive unit 306 is an electric circuit that outputs a drive signal such as a drive voltage for causing the line illuminating light source 60 to emit light in response to an input control signal.

The imaging element control unit 307 controls imaging by the imaging element 84 of the spectroscopic unit 80 in response to an input control signal. Also, imaging data generated by the imaging element 84 is transmitted to the HDD 309 via the imaging element control unit 307 to be stored in the HDD 309 as color data.

The motor drive unit 308 is an electric circuit that outputs drive signals such as drive voltages to respective motors for operating the paper conveying unit 30 and the color data acquiring unit conveying unit 40 in response to input control signals.

The control unit 300 implements the function of estimating the spectral characteristics of the paper 100 based on acquired color data using a transformation matrix.

Note that in some embodiments, a part or all of the control processes performed by the CPU 301 may be implemented by an electronic circuit such as an FPGA (Field-Programmable Gate Array) or an ASIC (Application Specific Integrated Circuit), for example.

Figure 5:
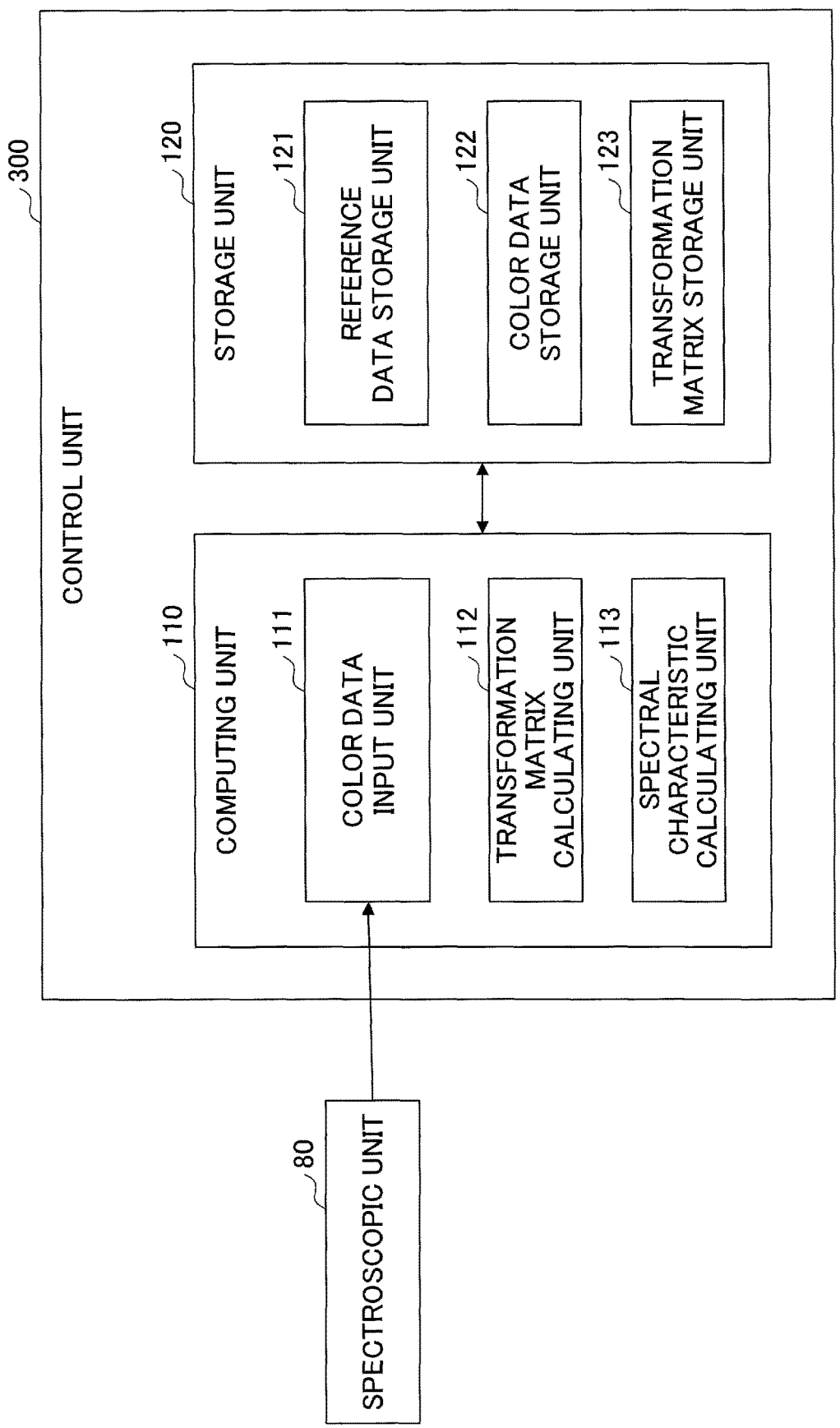
FIG. 5 is a block diagram illustrating an example functional configuration for spectral characteristic estimation computation by the spectral characteristic acquiring apparatus according to the first embodiment.

FIG. 5 is a block diagram illustrating an example functional configuration for spectral characteristic estimation computation.

The control unit 300 includes a computing unit 110 and a storage unit 120. The computing unit 110 includes a color data input unit 111, a transformation matrix calculating unit 112, and a spectral characteristic calculating unit 113. The storage unit 120 includes a reference data storage unit 121, a color data storage unit 122, and a transformation matrix storage unit 123. In the following, the functions of the above elements of the computing unit 110 and a method of estimating a spectral reflectance distribution as spectral characteristics of the paper 100 will be described.

In the spectral characteristic acquiring apparatus 10, when light is irradiated from the line illuminating light source 60 onto the paper 100, an electric signal is output from the imaging element 84 of the spectroscopic unit 80 that has received a diffraction image, and the output electric signal is input to the color data input unit 111 as color data.

When the color data is input, the spectral characteristic calculating unit 113 calculates the spectral characteristic of the paper 100 based on the input color data using a transformation matrix stored in advance in the transformation matrix storage unit 123. Note that the spectral characteristic calculating unit 113 is an example of a "spectral characteristic calculating unit".

In the following, a method of estimating a spectral reflectance distribution as spectral characteristics based on color data output by one spectral sensor included in the spectroscopic unit 80 will be described. Note, however, that spectral characteristics may also be obtained through methods that differ from the method described below.

Color data vi (i=1 to N) is acquired from N pixels constituting one spectral sensor of the spectroscopic unit 80, and the acquired color data vi is stored in a matrix V. Using the matrix V and a transformation matrix G, a matrix r storing the spectral reflectance of each wavelength band (e.g., wavelength range from 400 nm to 700 nm subdivided into 31 bands each with a 10-nm pitch) can be expressed by the following formula (1). Note that the transformation matrix G is an example of a "preset transformation matrix".

$$r = Gv \quad \text{[Formula 1]}$$

The transformation matrix G is obtained by minimizing the square of the norm $\|\cdot\|^2$ of an error using the least squares method based on a matrix R storing spectral reflectance distributions of a plurality (n) of known reference samples and the matrix V storing color data v obtained from the reference samples by a spectral sensor as indicated by the following formulas (2) to (4).

$$R = [r1, r2, \ldots, rn] \quad \text{[Formula 2]}$$

$$V = [v1, v2, \ldots, vn] \quad \text{[Formula 3]}$$

$$e = \|R - GV\|^2 \to \min \quad \text{[Formula 4]}$$

The transformation matrix G, as a regression equation from V to R with V as the explanatory variable and R as the objective variable, can be expressed by the following formula (5) using the Moore-Penrose generalized inverse matrix that gives the square of the least-norm solution of the matrix V, for example. Note that in formula (5), the superscript T represents the transpose of the matrix, and the superscript −1 represents the inverse matrix.

$$G = RV^T(VV^T)^{-1} \quad \text{[Formula 5]}$$

In the spectral characteristic acquiring apparatus 10, the result of acquiring the spectral reflectance of the reference samples is stored in advance in the reference data storage unit 121 of the control unit 300.

The transformation matrix calculating unit 112 generates a matrix $V_{ref}$ based on the color data obtained from the reference samples by the spectral characteristic acquiring apparatus 10. The transformation matrix calculating unit 112 also generates a matrix $R_{ref}$ based on the spectral reflectance distribution of the reference samples stored in the reference data storage unit 121. The transformation matrix calculating unit 112 calculates the transformation matrix G based on the generated matrices $V_{ref}$ and $R_{ref}$ using the above formula (5).

The transformation matrix G calculated by the transformation matrix calculating unit 112 is stored in the transformation matrix storage unit 123. The matrix $V_{ref}$ of color data obtained from the reference sample by the spectral characteristic acquiring apparatus 10 is stored in the color data storage unit 122 of the control unit 300.

When estimating the spectral characteristics of the paper 100, the spectral characteristic calculating unit 113 first generates a matrix $V_{exp}$ from the color data of the paper 100 and acquires the transformation matrix G stored in the transformation matrix storage unit 123. By using the matrix $V_{exp}$ and the transformation matrix G, the spectral characteristic calculating unit 113 can estimate spectral characteristics $R_{exp}$ of the paper 100 using the formula (2).

In the estimation computation described above, the plurality of reference samples used in calculating the transformation matrix G are preferably evenly selected from the color range (gamut) of a color space (e.g., XYZ color space or L*a*b* color space) that can be reproduced in a printed image. By using the transformation matrix G calculated based on such reference samples, the spectral characteristics of an image formed on the paper 100 may be estimated with high accuracy, for example.

However, the generation, maintenance, and measurement of reference samples require a substantial amount of time and costs. As such, the transformation matrix G is desirably obtained based on a small number of reference samples to the extent that the spectral characteristic estimation accuracy would not be substantially compromised.

Figure 6:
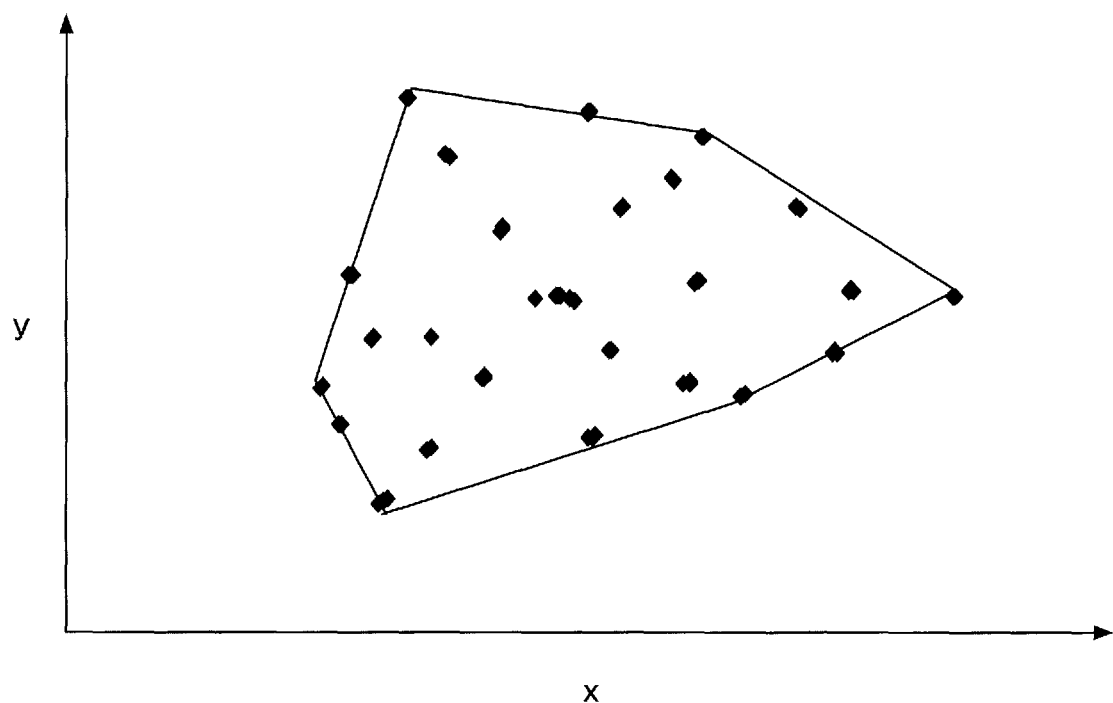
FIG. 6 is a diagram illustrating an example xy chromaticity distribution of reference samples and a color reproduction range of a toner image.

For example, toner images of 27 colors evenly selected from the reproducible color range of an electrophotographic image forming apparatus may be used as the reference samples. FIG. 6 is a graph indicating the xy chromaticity of each reference sample of the 27 colors. In FIG. 6, each point represents the xy chromaticity of a reference sample, and the solid line represents the color reproduction range of a toner image. FIG. 6 illustrates how the reference samples are evenly selected from the color reproduction range of the toner image.

In the spectral characteristic acquiring apparatus 10, the transformation matrix G calculated by the transformation matrix calculating unit 112 using the reference samples selected in the above-described manner is stored in advance in the transformation matrix storage unit 123.

In the following, operations of the color data acquiring unit 20 and the paper 100 at the time of color data acquisition by the spectral characteristic acquiring apparatus 10 will be described with reference to FIGS. 7A-7D. FIGS. 7A-7D are plan views of the paper 100 at the time of color data acquisition as viewed from the +Z-axis direction. FIGS. 7A-7D illustrate the paper 100 at different positions while being conveyed in the direction indicated by arrow 22 (i.e., +Y-axis direction).

In FIG. 7A, the color data acquiring unit 20 is positioned at the −X-axis direction end and the +Y-axis direction end of the paper 100. Starting from the position indicated in FIG. 7A, the color data acquiring unit 20 is continuously conveyed in direction 20a represented by the outlined arrow. Note that such continuous conveyance corresponds to a so-called scan drive. While the color data acquiring unit 20 is continuously conveyed, the spectroscopic unit 80 acquires color data of the color data acquiring region 21 of the paper 100 at predetermined time intervals. The predetermined time interval may be, for example, the frame period of the imaging element 84. At this time, conveyance of the paper 100 is stopped. When the spectroscopic unit 80 is conveyed to the +X-axis direction end of the paper 100, conveyance of the color data acquiring unit 20 is stopped.

Note that the paper 100 is detected to be at the color data acquiring position based on the output of the paper detection sensor 41 when the paper 100 and the paper detection sensor 41 are the positional arrangement as illustrated in FIG. 7A.

FIG. 7B illustrates the paper 100 after having been conveyed by a predetermined length in the Y-axis direction from the position illustrated in FIG. 7A. The predetermined length may be, for example, a length corresponding to the color data acquiring range of the spectroscopic unit 80 in the Y-axis direction. In FIG. 7B, the color data acquiring unit 20 is located at the +X-axis direction end of the paper 100.

Starting from the position illustrated in FIG. 7B, the color data acquiring unit 20 is continuously conveyed in direction 20b represented by the outlined arrows. While the color data acquiring unit 20 is continuously conveyed, the spectroscopic unit 80 acquires the color data of the color data acquiring region 21 of the paper 100 at predetermined time intervals. At this time, the conveyance of the paper 100 is stopped in the same manner as described above. When the color data acquiring unit 20 is conveyed to the −X-axis direction end of the paper 100, the conveyance of the color data acquiring unit 20 is stopped.

The color data acquiring unit 20 acquires color data of the color data acquiring region 21 of the paper 100 through similar operations in FIGS. 7C and 7D.

Note that the paper 100 is detected as having left the color data acquiring position based on the output of the paper detection sensor 41 when the paper 100 and the paper detection sensor 41 are in the positional arrangement as illustrated in FIG. 7D.

Through the operations as illustrated in FIGS. 7A-7D, color data of the entire region of the paper 100 can be acquired. Note that in the example described above, the color data acquiring unit 20 is conveyed four times in the X-axis direction to acquire color data of the entire region of the paper 100. However, the number of times the color data acquiring unit 20 is conveyed is not limited to a particular number and may be suitably determined based on the size of the paper 100.

Figure 8:
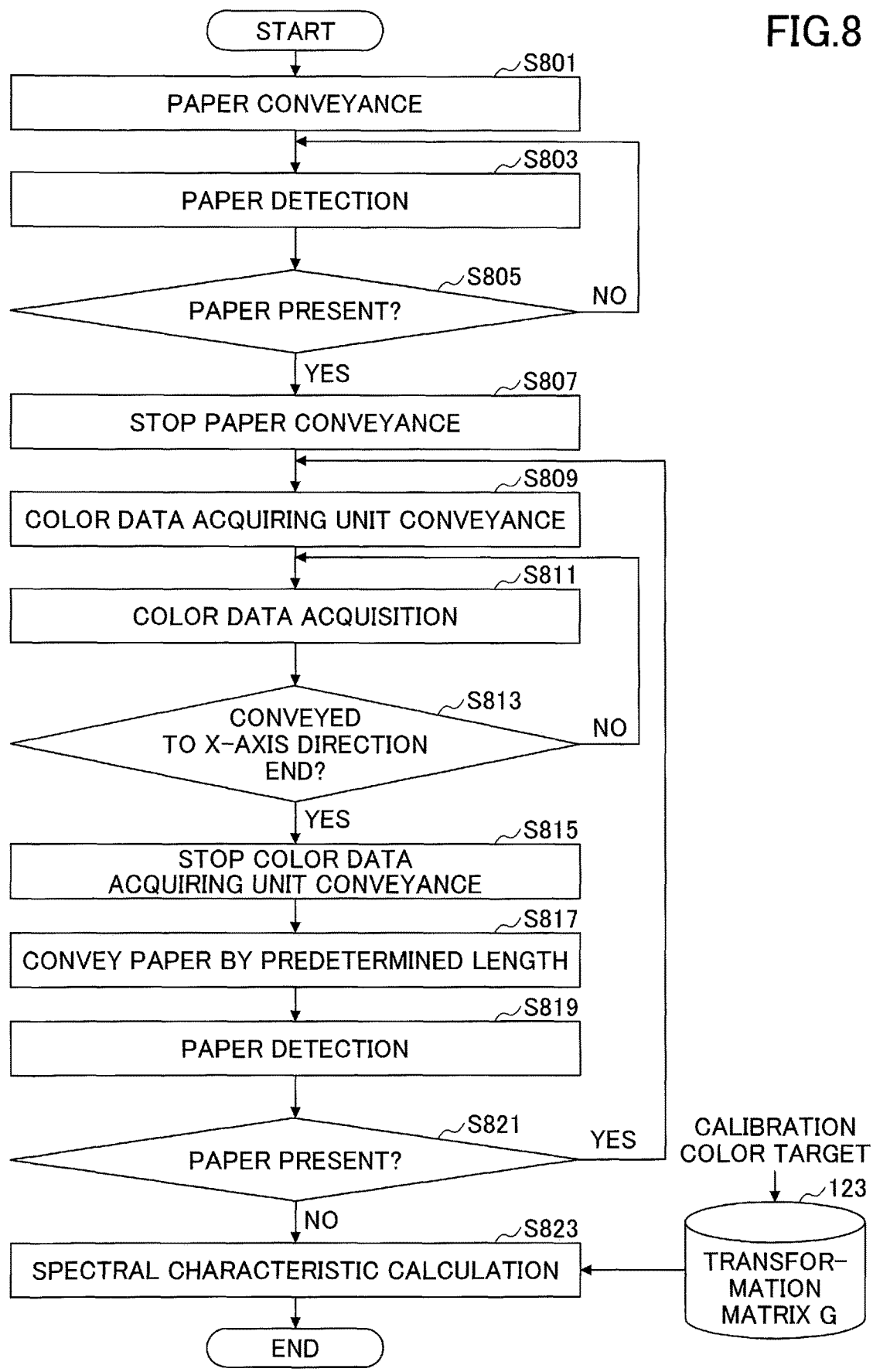
FIG. 8 is a flowchart illustrating an example spectral characteristic acquiring process by the spectral characteristic acquiring apparatus according to the first embodiment.

In the following, an example spectral characteristic acquiring process implemented by the spectral characteristic acquiring apparatus 10 will be described with reference to FIG. 8.

First, in step S801, the paper conveying unit 30 conveys the paper 100 in the Y-axis direction.

Then, in step S803, the paper detection sensor 41 acquires a detection signal indicating whether the paper 100 is at the color data acquiring position, and outputs the detection signal to the control unit 300.

Then, in step S805, the control unit 300 determines whether the paper 100 is located at the color data acquiring position based on the detection signal output by the paper detection sensor 41.

If it is determined in step S805 that the paper 100 is located at the color data acquiring position, the process proceeds to step S807 in which the paper conveying unit 30 stops conveying the paper 100 in the Y-axis direction. On the other hand, if it is determined in step S805 that the paper 100 is not at the color data acquiring position, the process returns to step S803.

Then, in step S809, the color data acquiring unit conveying unit 40 continuously conveys the color data acquiring unit 20 in the X-axis direction.

Then, in step S811, the color data acquiring unit 20 acquires color data at predetermined time intervals. That is, the imaging element 84 of the color data acquiring unit 20 acquires diffraction images generated from reflected light from the color data acquiring region 21 and outputs the diffraction images as color data.

Then, in step S813, the control unit 300 determines whether the color data acquiring unit 20 has been conveyed to the X-axis direction end of the paper 100. That is, the control unit 300 determines whether color data has been acquired across the entire X-axis direction color data acquiring range.

If it is determined in step S813 that the color data acquiring unit 20 has been conveyed to the X-axis direction end of the paper 100, the process proceeds to step S815 in which the color data acquiring unit conveying unit 40 stops conveyance of the color data acquiring unit 20. If it is determined in step S813 that the color data acquiring unit 20 has not been conveyed to the X-axis direction end of the paper 100, the process returns to step S811.

Then, in step S817, the paper conveying unit 30 conveys the paper 100 by a predetermined length in the Y-axis direction.

Then, in step S819, the paper detection sensor 41 acquires a detection signal indicating whether the paper 100 is at the color data acquiring position, and outputs the detection signal to the control unit 300.

Then, in step S821, the control unit 300 determines whether the paper 100 is at the color data acquiring position based on the detection signal output by the paper detection sensor 41.

If it is determined in step S821 that the paper 100 is located at the color data acquiring position, the process returns to step S809 and the acquisition of color data is continued. On the other hand, if it is determined in step S821 that the paper 100 is not at the color data acquiring position, the process proceeds to step S823 in which the spectral characteristic calculating unit 113 calculates the spectral characteristics of the paper 100 based on the acquired color data using the transformation matrix G stored in the transformation matrix storage unit 123.

By implementing the above-described process operations, the spectral characteristic acquiring process by the spectral characteristic acquiring apparatus 10 may be completed.

In this way, the spectral characteristic acquiring apparatus 10 conveys the paper 100 and acquires color data of the entire region of the paper 100 by conveying the color data acquiring unit 20, which has a plurality of spectroscopic sensors arranged in the conveying direction of the paper 100, in the width direction of the paper 100.

In the following, the calibration function of the spectral characteristic acquiring apparatus 10 for calibrating the transformation matrix G according to the present embodiment will be described. The calibration color target 50 is used for calibration of the transformation matrix. The transformation matrix stored in the transformation matrix storage unit 123 is calibrated using color data acquired by the color data acquiring unit 20 from the calibration color target 50. The calibration color target 50 is an example of a "calibration color target having a color target with known spectral characteristics".

The calibration color target 50 has color regions in different colors that are preferably evenly selected from a color range that is reproducible in an image (i.e., gamut) of a color space such as the XYZ color space or the L*a*b color space, for example.

As described above in connection with the reference samples used for calculating the transformation matrix G, the generation, maintenance, and measurement of the color regions of the calibration color target 50 require a substantial amount of time and costs. As such, a small number of color regions are preferably used to the extent that the estimation accuracy of spectral characteristics would not be compromised. In many cases, several to several tens of colors selected from the reproducible color range of image formation by an image forming apparatus are used. However, in order to increase the estimation accuracy of spectral characteristics and perform highly accurate measurement, several hundred to several thousand different colors may be required. Such a requirement is particularly relevant in the case where multicolor color materials of at least four colors are used for high image quality in image formation based on the electrophotographic method, the inkjet method, or the like, for example. Note that multicolor in the above context may include, for example, orange, green, white, clear, fluorescent colors, and the like, in addition to yellow, magenta, cyan, and black.

Figure 9:
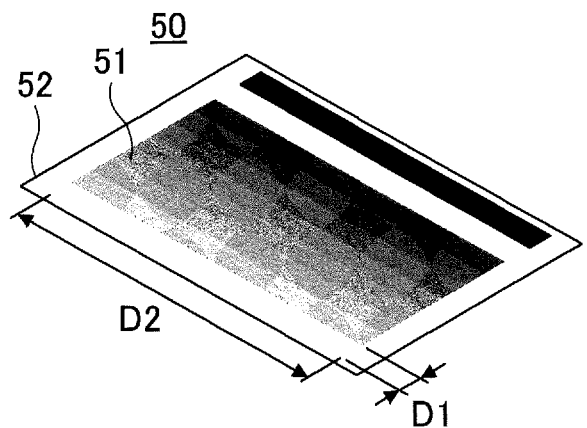
FIG. 9 is a diagram illustrating an example of a calibration color target of the spectral characteristic acquiring apparatus according to the first embodiment.

In the present embodiment, reference samples of several colors to several thousands of colors selected from the color reproducible range of image formation by an image forming apparatus are used in the calibration color target 50. FIG. 9 illustrates an example of the calibration color target 50 having such reference samples.

In FIG. 9, the calibration color target 50 includes a plate member 52 formed by cutting a metal material such as aluminum, for example, and a plurality of color targets 51 provided on the upper surface of the plate member 52. The color targets 51 are band-shaped members that are colored by color-adjusted paint or the like. The width D1 and the length D2 of each band are arranged so that the band is at least the size of a color data acquiring range of the spectroscopic unit 80 at one time of conveyance. For example, when the color data acquiring range of the spectroscopic unit 80 is 1 mm in the width direction and 100 mm in the conveying direction, the width D1 of the band may be arranged to be at least 1 mm and the length D2 of the band may be arranged to be at least 100 mm. The calibration color target 50 is configured by arranging such color targets 51 side-by-side in the width direction on the plate member 52 so that their length directions (longitudinal directions) are substantially parallel to the conveying direction.

The color targets 51 may be directly formed on the plate member 52, or color images may be formed on band-shaped paper which may then be attached to the plate member 52 as the color targets 51, for example. The plate member 52 is arranged to be large enough so that the color targets 51 would not be touched when held or conveyed. Note that when the color targets 51 are in a large number of different colors, the color targets 51 may be arranged on a plurality of plate members 52, for example.

Figure 10:
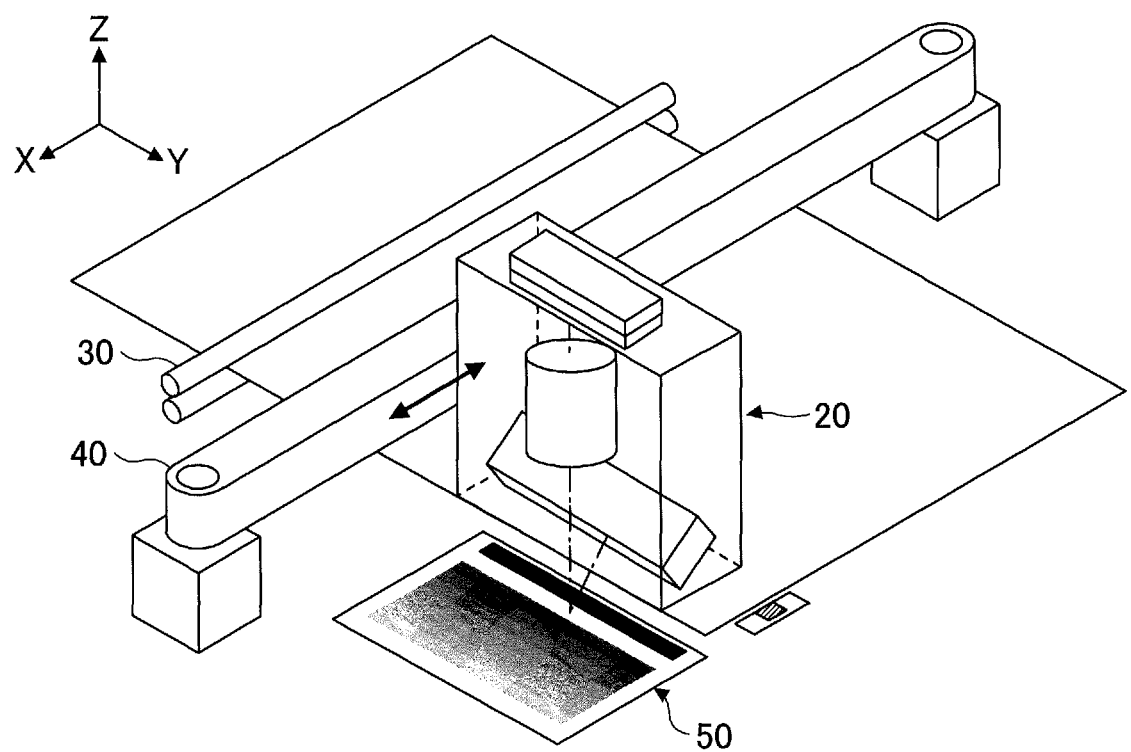
FIG. 10 is a perspective view diagram illustrating an example disposition of the spectroscopic unit when calibration is performed by the spectral characteristic acquiring apparatus according to the first embodiment.

As illustrated in FIG. 10, the calibration color target 50 is arranged adjacent to the paper 100 in the width direction of the paper 100 that is arranged within the conveyance range of the color data acquiring unit 20. That is, the calibration color target 50 is arranged within the conveyance range of the color data acquiring unit 20 conveyed by the color data acquiring unit conveying unit 40, at a region other than the region where the paper 100 is arranged. By conveying the color data acquiring unit 20 up to the position of the calibration color target 50, calibration using the calibration color target 50 may be performed.

The spectral characteristics of the color targets 51 of the calibration color target 50 are measured in advance using a highly accurate spectroscope, and a matrix $R_1$ representing the spectral characteristics of the color regions is stored in advance in the reference data storage unit 121.

In the following, a method of calibrating the transformation matrix G by the transformation matrix calculating unit 112 will be described. Note that each of the spectroscopic sensors included in the color data acquiring unit 20 has a transformation matrix G. The transformation matrix G of each spectroscopic sensor is calibrated by the transformation matrix calculating unit 112. Note that the transformation matrix calculating unit 112 is an example of a "transformation matrix calibrating unit".

When calibrating the transformation matrix G, the color data acquiring unit 20 moves to the position of the calibration color target 50. Light is irradiated from the line illuminating light source 60 onto the calibration color target 50, and each spectral sensor of the color data acquiring unit 20 captures a diffraction image and outputs color data.

First, the transformation matrix calculating unit 112 acquires, from the reference data storage unit 121, the matrix $R_{ref}$ representing the spectral characteristics of the reference samples measured in advance and the matrix $R_1$ representing the spectral characteristics of the color targets 51 of the calibration color target 50, and adds the matrix $R_1$ to the matrix $R_{ref}$ to obtain matrix $R_{rev}$. The transformation matrix calculating unit 112 also adds a matrix $V_1$ of the color data obtained from the color targets 51 to the matrix $V_{ref}$ of the color data obtained from the reference samples stored in the color data storage unit 122 to obtain a matrix $V_{rev}$.

Using the matrices $R_{rev}$ and $V_{rev}$ obtained in the above-described manner, the transformation matrix calculating unit 112 obtains a transformation matrix $G_1$ using the above formula (5), and saves the calibrated transformation matrix $G_1$ in the transformation matrix storage unit 123.

Figure 11:
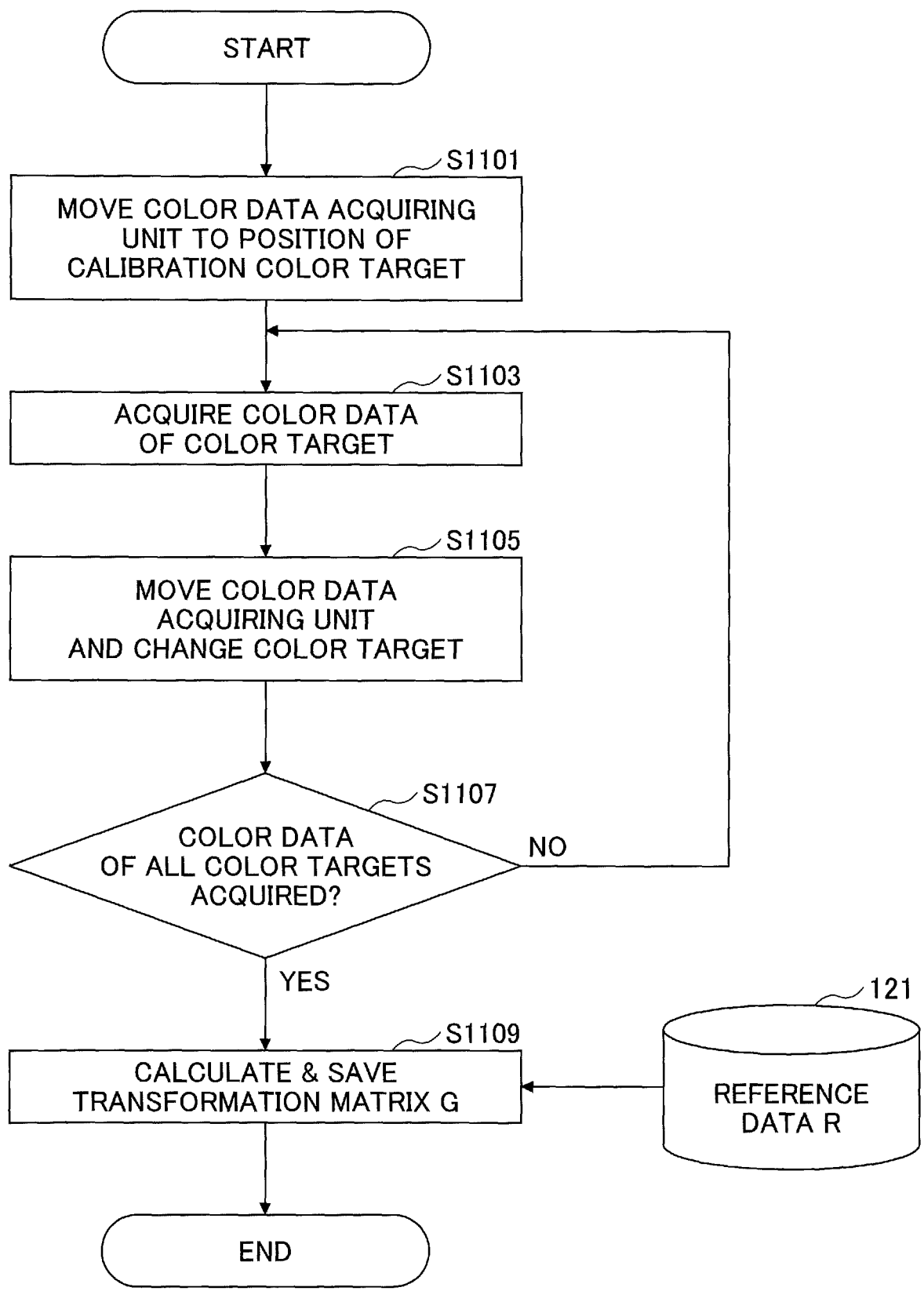
FIG. 11 is a flowchart illustrating an example transformation matrix calibration process performed by the spectral characteristic acquiring apparatus according to the first embodiment.

FIG. 11 is a flowchart illustrating an example of the calibration process as described above.

First, in step S1101, the color data acquiring unit conveying unit 40 conveys the color data acquiring unit 20 in the width direction of the paper 100, and moves the color data acquiring unit 20 to the position of the color target 51 located at the end of the calibration color target 50. For example, in FIG. 10, the color data acquiring unit 20 to the position may be moved to the position of the color target 51 at the −X-axis direction end of the calibration color target 50.

Then, in step S1103, the color data acquiring unit 20 acquires the color data of the color target.

Then, in step S1105, the color data acquiring unit conveying unit 40 conveys the color data acquiring unit 20 in the width direction to change the color target from which color data is to be acquired.

Then, in step S1107, the control unit 300 determines whether color data of all the color targets have been acquired.

If it is determined in step S1107 that color data of all the color targets have been acquired, the process proceeds to step S1109 in which the transformation matrix calculating unit 112 obtains the transformation matrix $G_1$ using the above formula (5), and stores the calibrated transformation matrix $G_1$ in the transformation matrix storage unit 123. FIG. 12 illustrates an example list of spectral characteristics acquired by each spectral sensor 80m in the color data acquiring unit 20 for each color target.

On the other hand, if it is determined in step S1107 that color data of all the color targets have not been acquired, the process returns to step S1103 to acquire color data of the next color target.

In this way, the calibrated transformation matrix $G_1$ may be obtained. By using the calibrated transformation matrix $G_1$, the spectral characteristic calculating unit 113 can estimate the spectral characteristics of the paper 100 more accurately.

As described above, according to an aspect of the present embodiment, the color data acquiring unit 20 is conveyed in the width direction, and as such, even when an image formed on the paper 100 has a large width, color data of the entire width of the image can be acquired without using an expensive light source that can illuminate the entire width of the image at once. In this way, the spectral characteristic acquiring apparatus 10 according to the present embodiment that can acquire spectral characteristics with high accuracy without using an expensive light source may be provided at a low cost.

Further, by arranging a plurality of spectroscopic sensors in the conveying direction of the paper 100, spectral characteristics of the paper 100 across a wide range in the conveying direction may be acquired at once, for example. Further, by promoting cooperation between the conveyance of the color data acquiring unit 20 and the conveyance of the paper 100, spectral characteristics of wide area of the paper 100 may be promptly acquired.

Also, by calibrating the transformation matrix using the calibration color target 50, temporal changes in the spectral characteristic acquisition accuracy due to changes in air temperature, wavelength characteristics of the light source, and the like may be reduced.

Further, according to an aspect of the present embodiment, the calibration color target 50 is arranged within the conveyance range of the color data acquiring unit, at a region other than the region where the paper 100 is arranged. In this way, switching between spectral characteristic acquisition mode and calibration mode may be enabled by simply moving the color data acquiring unit 20. Thus, calibration may be easily performed without providing a complicated configuration or mechanism for mode switching. Note that the color data acquiring unit conveying unit 40 that moves the color data acquiring unit 20 to the position of the calibration color target 50 is an example of a "mode switching unit".

Also, by arranging the band-shaped color targets 51 such that their longitudinal directions are substantially parallel to the conveying direction of the paper 100, a plurality of the spectral sensors of the color data acquiring unit 20 may be calibrated at once and calibration may be efficiently performed.

Second Embodiment

In the following, an example spectral characteristic acquiring apparatus according to a second embodiment of the present invention will be described. Note that features of the second embodiment that are substantially identical to those of the first embodiment are given the same reference numerals and their descriptions may be omitted.

In the spectral characteristic acquiring apparatus, characteristics of the line illuminating light source 60 may change due to influences of environmental change such as temperature change or deterioration over time, and color data acquired by the color data acquiring unit 20 for the same paper 100 may change over time.

In this respect, the calibration color target 50 used by a spectral characteristic acquiring apparatus 10a according to the present embodiment includes a white color target and a black color target, and a correction coefficient calculating unit of the spectral characteristic acquiring apparatus 10a calculates a color data correction coefficient using these color targets. In the present embodiment, the spectral characteristic calculating unit 113 estimates the spectral characteristics of the paper 100 using acquired color data that is by multiplied by the color data correction coefficient obtained by the correction coefficient calculating unit so that the spectral characteristics may always be estimated with high accuracy irrespective of changes in the line illuminating light source 60 and the like.

Note that backing conditions are determined based on the purpose. For example, black backing may be used for ISO compliance and calibration, and white backing may be used for color profile creation for printing. The term "backing" refers to the backing color at the time of measurement. A white color target corresponding to a color target that is entirely white is used as the white backing, and a black color target corresponding to a color target that is entirely black is used as the black backing. The white color target may be a white film, white printing paper or the like, for example, and the black color target may be a black film, black printing paper, or the like, for example. In the present embodiment, the white color target and the black color target are included in the plurality of color targets of the calibration color target 50. Thus, the color data acquiring unit 20 can acquire color data for obtaining the correction coefficient by moving to the position of the white color target or the black color target in the calibration color target 50.

Note that reference color data $v_{wref}$ and reference color data $v_{bref}$ respectively obtained from the white color target and the black color target are measured in advance and stored in the color data storage unit 122 as reference values.

Figure 13:
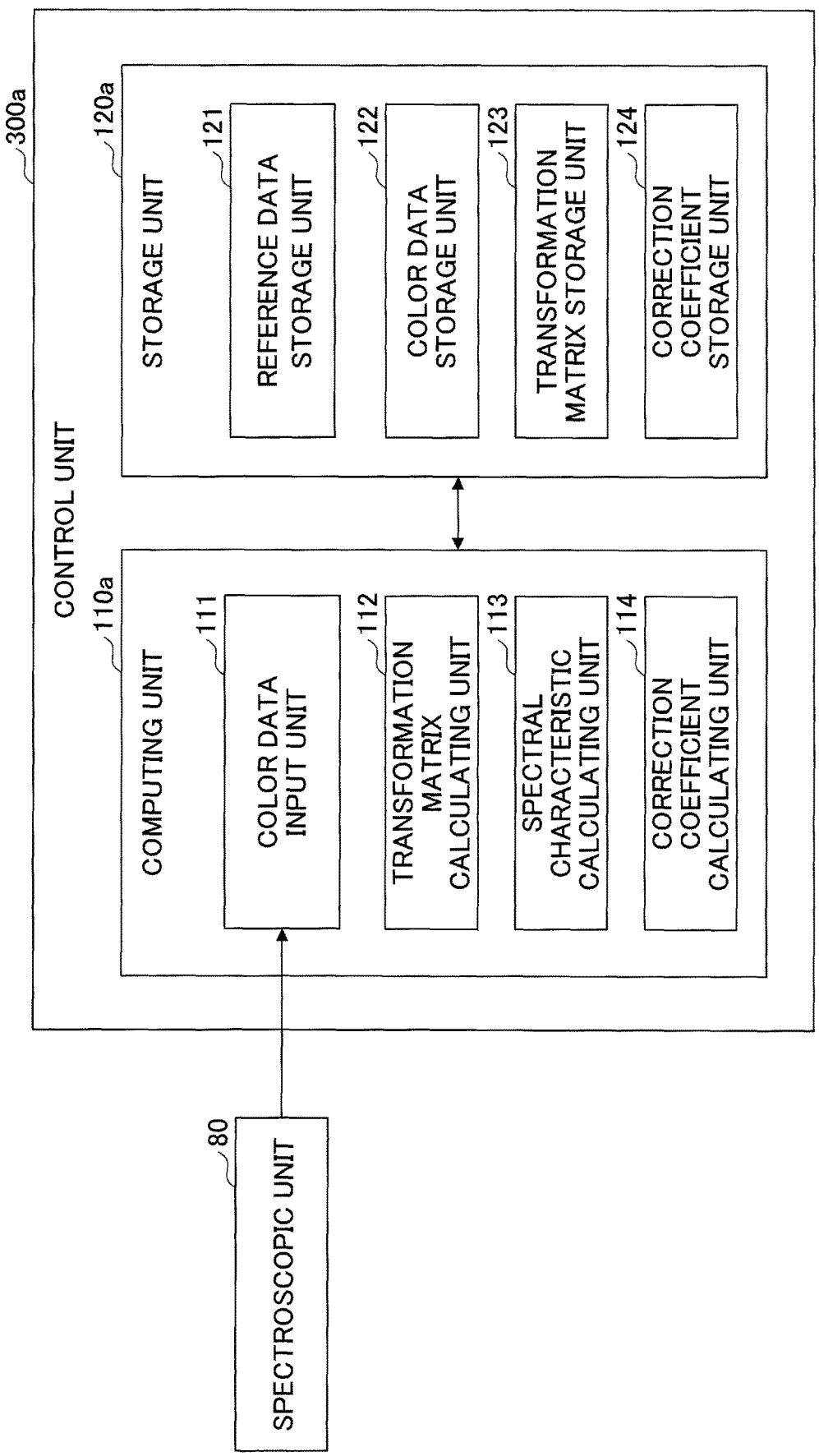
FIG. 13 is a block diagram illustrating an example functional configuration for correction coefficient acquisition calculation by the spectral characteristic acquiring apparatus according to a second embodiment of the present invention.

FIG. 13 illustrates an example functional configuration of the spectral characteristic acquiring apparatus 10a according to the present embodiment. The spectral characteristic acquiring apparatus 10a includes a control unit 300a that includes a calculating unit 110a including a correction coefficient calculating unit 114 and a storage unit 120a including a correction coefficient storage unit 124.

The correction coefficient calculating unit 114 acquires color data $v_w$ and color data $v_b$ from the white color target and the black color target. The correction coefficient calculating unit 114 also acquires the reference color data $v_{wref}$ and the reference color data $v_{bref}$ from the color data storage unit 122. The correction coefficient calculating unit 114 calculates correction coefficients w and b using the following formulas (6) and (7).

$$w_i = v_{wref \cdot i} / v_{w \cdot i} \ (i=1,2,\ldots,N) \quad (6)$$

$$b_i = v_{bref \cdot i} / v_{b \cdot i} \ (i=1,2,\ldots,N) \quad (7)$$

The correction coefficient calculating unit 114 stores the correction coefficients w and b in the correction coefficient storage unit 124.

In the case of estimating the spectral characteristics of the paper 100, when the spectral characteristic calculating unit 113 acquires color data v of the paper 100, the spectral characteristic calculating unit 113 calculates corrected color data v' of the paper 100 using the correction coefficients w and b acquired from the correction coefficient storage unit 124, based on the following formulas (8) and (9).

$$v_w' = w \cdot v \quad (8)$$

$$v_b' = b \cdot v \quad (9)$$

In the case of white backing, the spectral characteristic calculating unit 113 generates a matrix $V_{exp}$ based on the corrected color data $v_w'$ based on the above formula (8), and estimates the spectral characteristics $R_{exp}$ of the paper 100 using the transformation matrix G stored in the transformation matrix storage unit 123 based on the above formula (1).

In the case of black backing, the spectral characteristic calculating unit 113 generates a matrix $V_{exp}$ based on the corrected color data $v_b'$ based on the above formula (9), and estimates the spectral characteristics $R_{exp}$ of the paper 100 using the transformation matrix G stored in the transformation matrix storage unit 123 based on the above formula (1).

Figure 14:
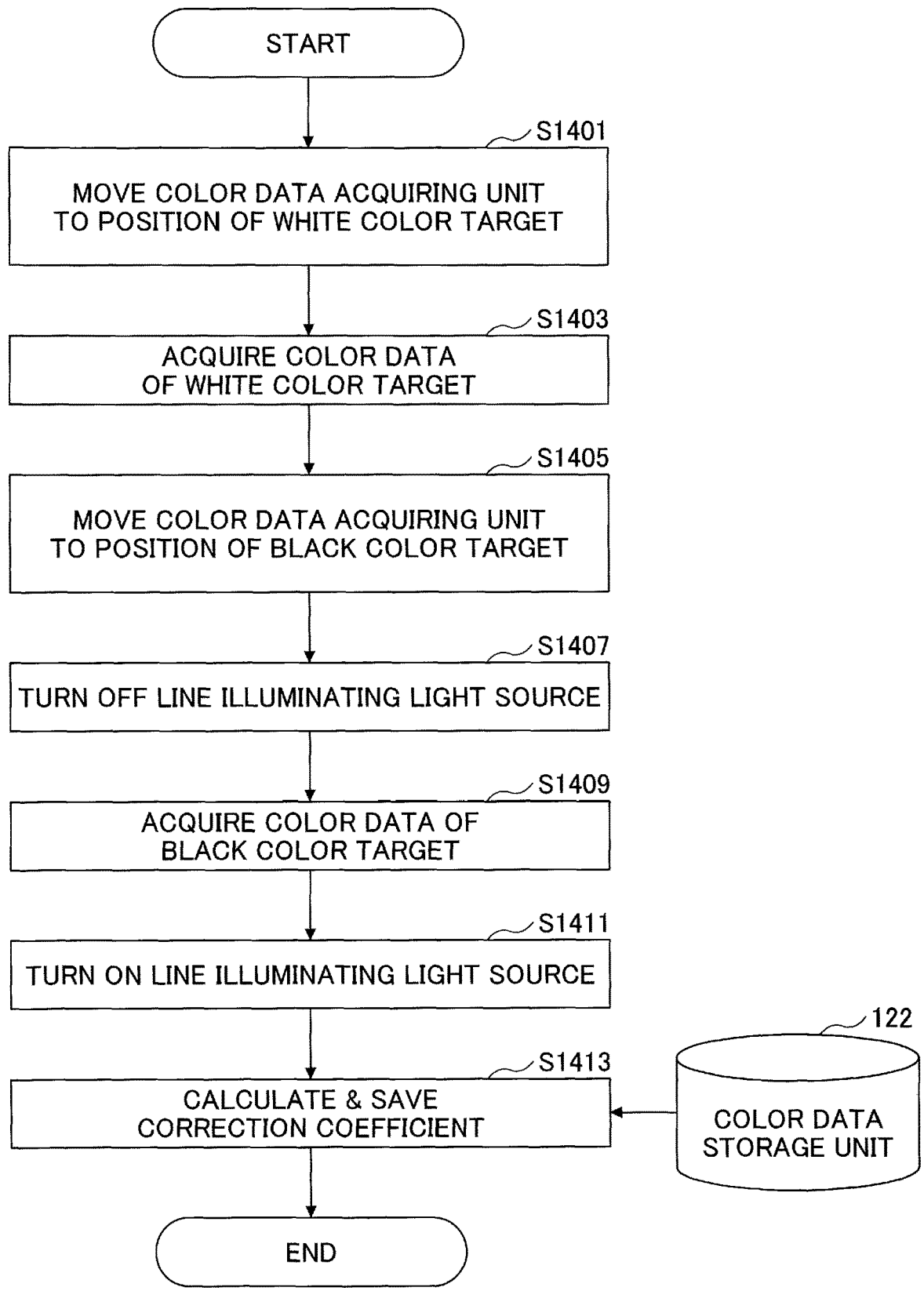
FIG. 14 is a flowchart illustrating an example correction coefficient acquiring process performed by the spectral characteristic acquiring apparatus according to the second embodiment.

FIG. 14 is a flowchart illustrating an example process of acquiring correction coefficients for color data. First, in step S1401, the color data acquiring unit conveying unit 40 moves the color data acquiring unit 20 to the position of the white color target of the calibration color target 50.

Then, in step S1403, the color data acquiring unit 20 acquires color data $v_w$ of the white target.

Then, in step S1405, the color data acquiring unit conveying unit 40 moves the color data acquiring unit 20 to the position of the black target of the calibration color target 50.

Then, in step S1407, the control unit 300 turns off the line illuminating light source 60 via the light source drive unit 306. Note that the line illuminating light source 60 is turned off in order to acquire output of color data from dark current. Dark current is the current that flows when light is not irradiated onto the pixels of the imaging element 84. For example, when the temperature rises by 7° C. to 10° C., the dark current is approximately doubled.

Then, in step S1409, the color data acquiring unit 20 acquires color data $v_b$ of the black target.

Then, in step S1411, the control unit 300 turns on the line illuminating light source 60 via the light source drive unit 306. The line illuminating light source 60 is turned on at this time to prepare for the acquisition of the next color data.

Then, in step S1413, the correction coefficient calculating unit 114 refers to the color data storage unit 122 to acquire the reference color data $v_{wref}$ and the reference color data $v_{bref}$, calculates correction coefficients w and b using the above formulas (6) and (7), and stores the calculated correction coefficients w and b in the correction coefficient storage unit 124.

In this way, the spectral characteristic acquiring apparatus 10a can calculate and store the correction coefficients w and b using the white color target and the black color target. The white color target is an example of "white color target", and the black color target is an example of "black color target".

As described above, in the present embodiment, color data output by the color data acquiring unit 20 is corrected so as to prevent degradation of spectral characteristic estimation accuracy caused by changes in the line illuminating light source 60 and the like. In this way, spectral characteristics may always be estimated with high accuracy.

Note that correction of changes occurring over a relatively short time period may serve as a simple calibration. According to the present embodiment, such simple calibration can be implemented without complicated operations.

In the above description, simple calibration has been described as a function separate from the spectral characteristic acquiring function. However, because such simple calibration can be easily performed by moving the color data acquiring unit 20, the simple calibration may alternatively be performed each time spectral characteristics are acquired as a part of the spectral characteristic acquiring process, for example. In this way, acquisition accuracy may always be ensured when acquiring spectral characteristics.

Note that other advantageous effects described above in connection with the first embodiment may similarly be obtained in the second embodiment.

Third Embodiment

In the following, an example image forming apparatus that includes the spectral characteristic acquiring apparatus according to the first embodiment or the second embodiment and is configured to acquire in-line spectral characteristics and adjust image forming conditions and the like will be described. Note that in the following description of the third embodiment, descriptions of features already described above in connection with the first embodiment or the second embodiment may be omitted.

Figure 15:
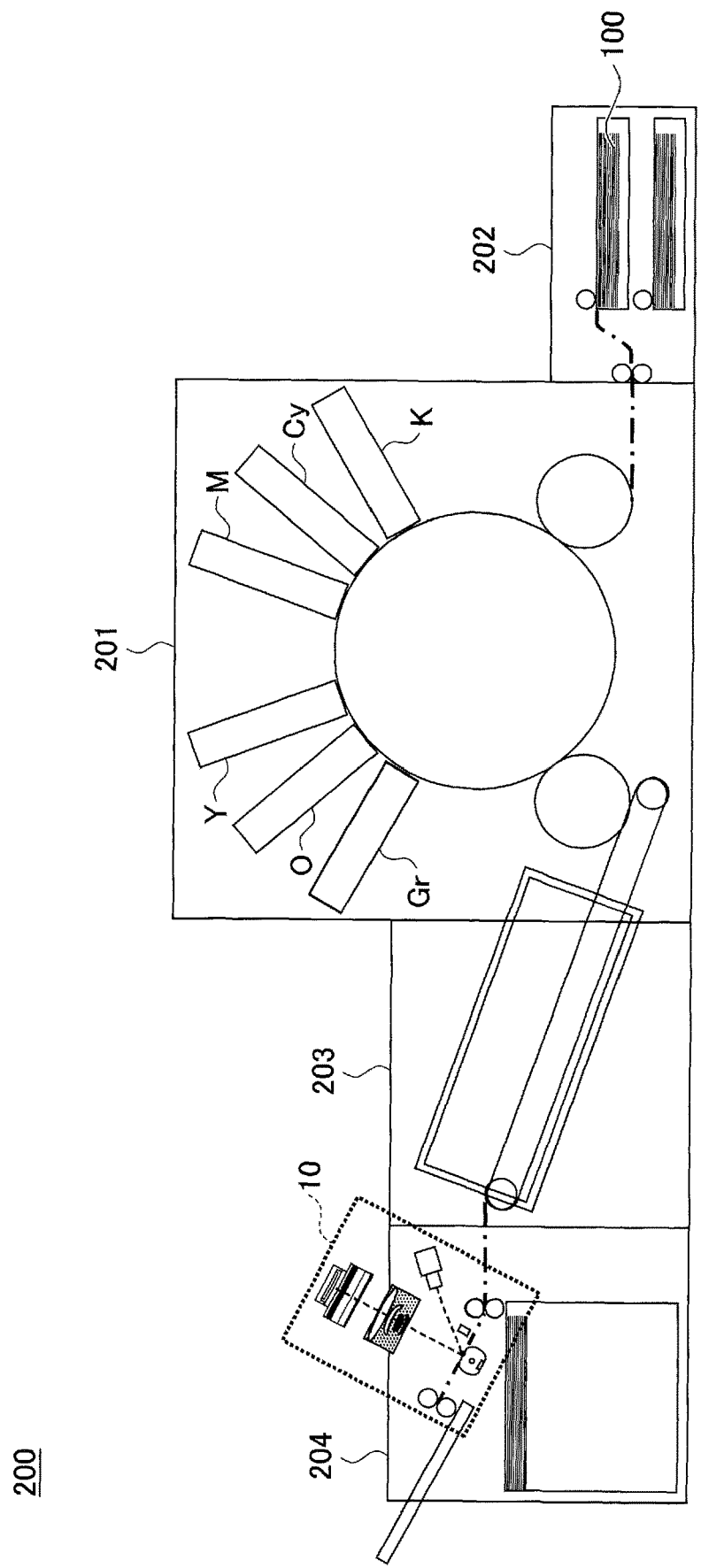
FIG. 15 is a diagram illustrating an example configuration of an image forming apparatus according to a third embodiment of the present invention.

FIG. 15 illustrates an example configuration of an image forming apparatus 200 according to the third embodiment.

The image forming apparatus 200 according to the present embodiment is an inkjet image forming apparatus including the spectral characteristic acquiring apparatus 10, an image forming unit 201, a paper feeding unit 202, a drying unit 203, and a paper discharge unit 204. The image forming unit 201 has inkjet heads Gr, O, Y, M, Cy, and K arranged therein. Note that the symbols Gr, O, Y, M, Cy, and K represent ink colors of green, orange, yellow, magenta, cyan, and black, respectively.

The paper feeding unit 202 of the image forming apparatus 200 accommodates sheets of the paper 100 corresponding to the object of spectral characteristic acquisition. The paper 100 may be fed in order from the uppermost sheet of paper 100 in the paper feeding unit 202 and conveyed to the image forming unit 201 at the appropriate timing by a pair of rollers, for example.

The image forming unit 201 applies ink to the paper 100 using inkjet heads of corresponding colors to form a visible image based on image information. After ink is applied to the paper 100, the paper 100 is transported to the drying unit 203, and the ink is dried while the paper is conveyed across the drying unit 203. The dried paper 100 is then discharged by the paper discharge unit 204 or accommodated in a stacker.

The spectral characteristic acquiring apparatus 10 is arranged in the paper discharge unit 204 so as to face an image surface of the paper 100. Note that the image surface of the paper 100 is an example of a "recording medium surface". The spectral characteristic acquiring apparatus 10 is used to conduct periodic inspections at the time the image forming apparatus 200 is activated, when the type of paper is changed, and/or when the image forming apparatus 200 is operated for a long time, for example. The spectral characteristic acquiring apparatus 10 acquires the spectral characteristics of the image data on the paper 100 while the paper 100 is being discharged and monitors color unevenness and color variations within the image formed on the paper surface.

The data acquired by the spectral characteristic acquiring apparatus 10 is sent to a control unit of the image forming apparatus 200. The control unit functions as an image evaluating apparatus and adjusts image forming conditions such as the amount of ink applied by the inkjet heads and the like based on evaluation results for improving color reproducibility.

Note that in the above-described example, the spectral characteristic acquiring apparatus 10 according to the first embodiment is used in the image forming apparatus 200. However, the spectral characteristic acquiring apparatus 10a according to the second embodiment may be used instead of the spectral characteristic acquiring apparatus 10, for example.

Note that various types of image forming apparatus products are available on the market including printers, copying machines, multifunction peripherals as high added-value products having communication functions in addition to image forming functions, commercial printing machines, and the like. Also, various image forming methods are available including electrophotographic methods, inkjet methods, heat sensitive methods, and the like.

Even in the field of production printing, digitization of both sheet-fed presses and continuous feed printers are progressing, and various products using electrophotographic methods and inkjet methods are available on the market.

Also, there are increasing user needs for multidimensionality, high definition, and high density of images in view of the transition from monochrome printing to color printing. Further, with the diversification of services delivered to consumers, such as high-quality photographic printing, catalog printing, inclusion of personalized advertisement according to personal preferences in invoices and the like, there are growing demands for high image quality, personal information security, and color reproducibility.

In the field of electrophotography, techniques are known for achieving higher image quality by installing a toner density sensor for detecting the toner density of toner before being fixed to an intermediate transfer medium or a photoreceptor to stabilize the toner supply amount.

In the field of personal information security, regardless of the specific image forming method, techniques are known for inspecting images by capturing an output image with a camera or the like and performing character recognition or difference detection by inter-image difference calculation and the like.

In the field of color reproduction, products are available on the market that uses a spectral characteristic acquiring apparatus such as a spectroscopic measurement apparatus or the like to acquire spectral characteristics of one or more points to perform calibration, for example.

In the present embodiment, the spectral characteristic acquiring process is preferably carried out with respect to the entire region of the image formed by the image forming apparatus in order to appropriately respond to image fluctuations between pages and within a page.

Note that although the spectral characteristic acquiring apparatus 10 is provided inside the image forming apparatus 200 in the above-described example, the spectral characteristic acquiring apparatus 10 may be provided separately from the image forming apparatus 200 to configure an image forming system, for example. That is, an image forming system that is capable of acquiring spectral characteristics offline and evaluating the acquired spectral characteristics may be configured.

In this case, the image forming apparatus 200 may form images on one or more sheets of paper. Then, the sheets of paper having the images formed thereon may be brought to the position where the spectral characteristic acquiring apparatus 10 is located by a user, for example. Then, the spectral characteristic acquiring apparatus 10 may acquire the spectral characteristics of the image formed on each sheet of paper. The acquired spectral characteristics may then be fed back to the image forming apparatus 200 offline, and image forming conditions and imaging conditions of the image forming apparatus may be adjusted based thereon.

Fourth Embodiment

In the following, an example image forming apparatus management system according to a fourth embodiment of the present invention that includes the spectral characteristic acquiring apparatus according to the first embodiment or the second embodiment and is configured to manage an image forming apparatus will be described. In the following description of the fourth embodiment, descriptions of features that have already been described above in connection with the first embodiment or the second embodiment may be omitted.

Figure 16:
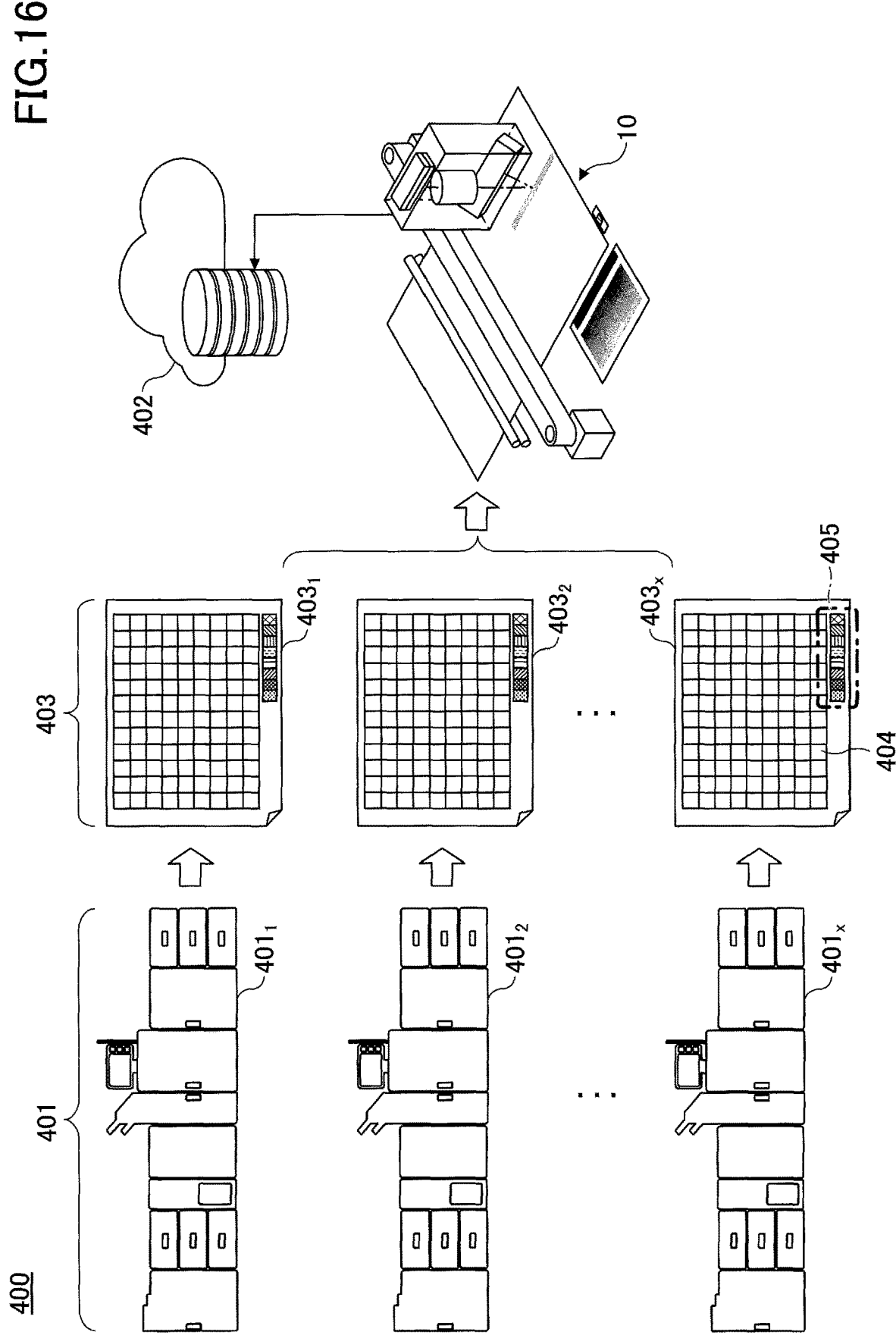
FIG. 16 is a diagram illustrating an example configuration of an image forming apparatus management system according to a fourth embodiment of the present invention.

FIG. 16 illustrates an example configuration of an image forming apparatus management system 400 according to the present embodiment. The image forming apparatus management system 400 includes the spectral characteristic acquiring apparatus 10, a plurality of image forming apparatuses $401_1$ to $401_x$, and a management server 402.

The image forming apparatuses $401_1$ to $401_x$ are inkjet image forming apparatuses.

The spectral characteristic acquiring apparatus 10 is used to conduct periodic image quality inspections of the image forming apparatuses $401_1$ to $401_x$ when they are activated, when the paper type is changed, when they are operated for a long time, and the like. The spectral characteristic acquiring apparatus 10 acquires spectral characteristics of images respectively formed on paper $403_1$ to $403_x$ by the image forming apparatuses $401_1$ to $401_x$ and monitors color unevenness and color variations in the images formed by the image forming apparatuses $401_1$ to $401_x$.

Upon image quality inspection, the image forming apparatuses $401_1$ to $401_x$ form color patches $404_1$ to $404_x$ as spectral characteristic acquisition images on the paper $403_1$ to $403_x$. In addition to forming the color patches $404_1$ to $404_x$, the image forming apparatuses $401_1$ to $401_x$ form color codes $405_1$ to $405_x$ on pre-designated regions of the paper $403_1$ to $403_x$.

In the following description, the image forming apparatuses $401_1$ to $401_x$ may be collectively referred to as "image forming apparatus 401". Also, the paper $403_1$ to $403_x$ may be collectively referred to as "paper 403", the color patches $404_1$ to $404_x$ may be collectively be referred to as "color patch 404", and the color codes $405_1$ to $405_x$ may be collectively be referred to as "color code 405".

The color patch 404 has a plurality of different colored figures two-dimensionally arranged therein and is used as a color reference. By acquiring the spectral characteristics of the color patches $404_1$ to $404_x$ formed by the image forming apparatuses $401_1$ to $401_x$, the spectral characteristics of images formed by the image forming apparatuses $401_1$ to $401_x$ can be evaluated. Ideally, all of the color patches $404_1$ to $404_x$ formed by the image forming apparatuses $401_1$ to $401_x$ are the same. However, due to differences in image forming characteristics of the image forming apparatuses $401_1$ to $401_x$, the acquired spectral characteristics of the color patches $404_1$ to $404_x$ may be slightly different from each other. Note that the color patch 404 is an example of a "predetermined pattern".

Figure 17:
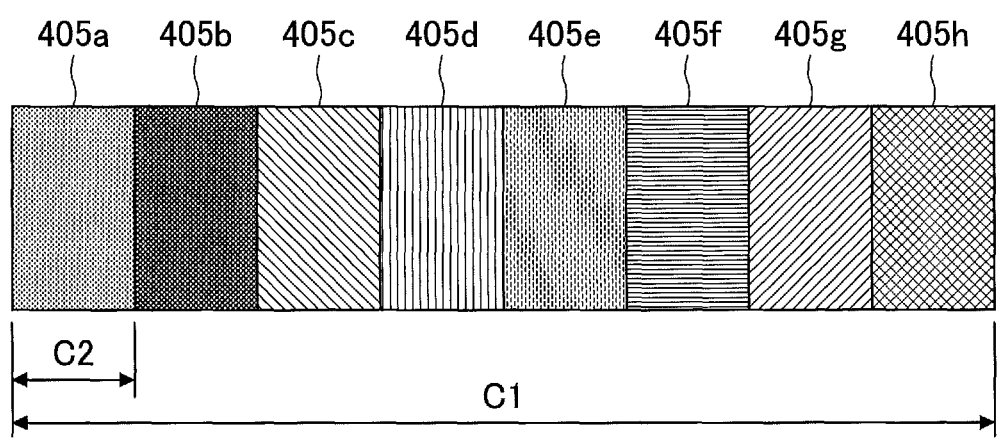
FIG. 17 is a diagram illustrating an example color code used in the image forming apparatus management system according to the fourth embodiment.

The color code 405 includes colored figures for representing identification information. The color code 405 has the colored figures in unique colors one-dimensionally arranged into a row. FIG. 17 schematically illustrates an example of the color code 405. In FIG. 17, textures $405a$ to $405h$ represent colored figures in different colors. Note that the color code 405 is an example of "identification information for identifying the image forming apparatus".

Note that the color of one colored figure may be represented by the mix ratio of red, blue, and green, for example. Thus, for example, by expressing the mix ratio of red, blue, and green in hexadecimal digits and converting it into a numerical value, the color code 405 can be used as identification information including various items of information.

Example items of information that may be represented by the color code 405 include the model name of the image forming apparatus 401, the product number of the image forming apparatus 401, the date/time the color code 405 was formed, the number of sheets of paper on which the color code 405 was formed, and the like.

Note that an overall size C1 of the color code 405 in the paper conveying direction is preferably set up so that the color code 405 would be within the color data acquiring range of the spectral characteristic acquiring apparatus 10. Also, a size C2 of one colored figure in the color code 405 is preferably arranged to be greater than the color data acquiring range of one spectral sensor included in the color data acquiring unit 20.

The paper $403_1$ to $403_x$ on which the image forming apparatuses $401_1$ to $401_x$ have formed images are passed to one spectral characteristic acquiring apparatus 10. The spectral characteristic acquiring apparatus 10 acquires the spectral characteristics of the color patches $404_1$ to $404_x$ respectively formed on the paper $403_1$ to $403_x$. Also, the spectral characteristic acquiring apparatus 10 acquires the spectral characteristics of the color codes $405_1$ to $405_x$ respectively formed on the paper $403_1$ to $403_x$ to acquire identification information. The spectral characteristic data and the identification information represented by the color codes 405 are associated with each other and stored in the management server 402. Note that the management server 402 is an example of a "storage apparatus configured to store identification information for identifying an image forming apparatus and spectral characteristics of a pattern in association with each other".

Figure 18:
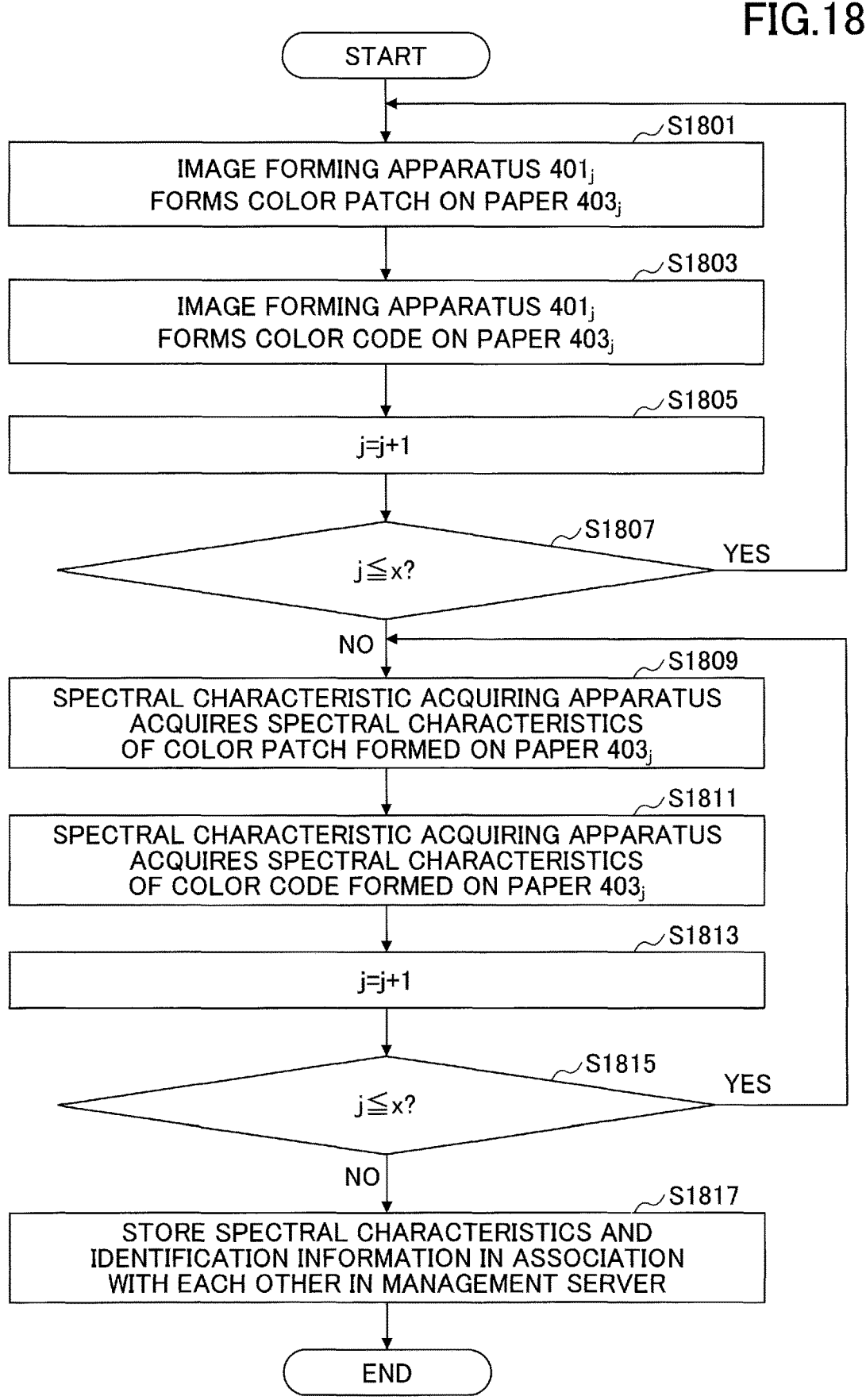
FIG. 18 is a flowchart illustrating an example process of an image forming apparatus management method implemented by the image forming apparatus management system according to the fourth embodiment.

FIG. 18 is a flowchart illustrating example process steps of an image forming apparatus management method implemented by the image forming apparatus management system according to the present embodiment.

First in step S1801, an image forming apparatus $401_j$ forms a color patch $404_j$ on paper $403_j$. Note that 'j' represents a natural number from 1 to x and may be a counter counting the number of image forming apparatuses 401 or a counter counting the number of sheets of paper 403. Also, 'x' represents the number of image forming apparatuses 401 included in the image forming apparatus management system 400. Note that step S1801 is an example of a "pattern forming step".

Then, in step S1803, the image forming apparatus $401_j$ forms a color code $405_j$ on the paper $403_j$.

Then, in step S1805, the counter j counting the number of image forming apparatuses 401 is incremented by one. Note that such updating of the counter j may be performed by the management server 402, for example. Alternatively, the counter J may be updated by a user using the image forming apparatus, for example.

Then, in step S1807, a determination is made as to whether j is less than or equal to x (j≤x). That is, a determination is made as to whether all the image forming apparatuses 401 have formed color patches 404 and color codes 405 on paper 403. Such a determination may be made by the management server 402, for example. Alternatively, the determination may be made by the user using the image forming apparatus, for example.

If it is determined in step S1807 that j is less than or equal to x (j≤x), the process returns to step S1801. On the other hand, if it is determined in step S1807 that j is not less than or equal to x, the process proceeds to step S1809 in which the spectral characteristic acquiring apparatus 10 acquires spectral characteristics of the color patch $404_j$ of the paper $403_j$.

Then, in step S1811, the spectral characteristic acquiring apparatus 10 acquires the identification information represented by the color code $405_j$ formed on the paper $403_j$.

Then, in step S1813, the counter j counting the number of sheets of paper 403 is incremented by one. Such updating of the counter j may be performed by the management server 402, for example. Alternatively, the counter j may be updated by a user using the image forming apparatus, for example.

Then, in step S1815, a determination is made as to whether j is less than or equal to x (j≤x). That is, a determination is made as to whether the spectral characteristic acquiring apparatus 10 has acquired the spectral characteristics of all the color patches 404 and the identification information of all the color codes 405 of all the sheets of paper 403. Such a determination is made by the management server 402, for example. Alternatively, the determination may be made by the user using the image forming apparatus, for example.

If it is determined in step S1815, if it is determined that j is less than or equal to x (j≤x), the process returns to step S1809. On the other hand, if it is determined in step S1815 that j is not less than or equal to x, the process proceeds to step S1817 in which the management server 402 stores the spectral characteristics of the color patches 404 and the identification information of the color codes 405 in association with each other. Note that step S1817 is an example of a "storage step".

In this way, the spectral characteristics of the color patches 404 and the identification information of the color codes 405 are stored in association with each other in the management server 402.

According to an aspect of the present embodiment, for example, a user can refer to the management server 402 to check the spectral characteristic data of an image forming apparatus 401 identified by it corresponding identification information. Also, the spectral characteristic data of each image forming apparatus 401 represented by its corresponding identification information may be acquired from the management server 402, and the image forming conditions of each image forming apparatus may be adjusted based on the acquired spectral characteristic data, for example.

Note that although inkjet image forming apparatuses are being managed in the above-described example, the present embodiment may be applied to various types of image forming apparatuses including those using electrophotographic methods, for example.

Although the spectral characteristic acquiring apparatus, the image forming apparatus, the image forming system, the image forming apparatus management system, and the image forming apparatus management method according to the present invention have been described above with respect to certain illustrative embodiments, the present invention is not limited to the above-described embodiments and various modifications and changes may be made within the scope of the present invention.

What is claimed is:

1. A spectral characteristic acquiring apparatus comprising:
   a plurality of spectral sensors configured to receive reflected light from a surface of a conveyed object that has been irradiated with light to acquire color data of the conveyed object;
   a first conveyor configured to convey the conveyed object in a predetermined conveying direction; and
   a second conveyor configured to convey the plurality of spectral sensors in a direction intersecting the predetermined conveying direction;
   a processor; and a memory storing program instructions that cause the processor to
estimate spectral characteristics of the conveyed object based on the acquired color data of the conveyed object using a preset transformation matrix,
wherein
the plurality of spectral sensors are arrayed in the predetermined conveying direction, and
each spectral sensor of the plurality of spectral sensors includes
an aperture, formed in an aperture array, and
a lens, provided in a lens array, wherein
the aperture array is arranged below the lens array in a direction that is orthogonal to the irradiated surface of the conveyed object,
the lens of each spectral sensor is arranged at a position corresponding to the aperture formed in the aperture array, and has a diameter such that all light transmitted through the corresponding aperture is incident upon the lens.

2. The spectral characteristic acquiring apparatus according to claim 1, wherein the program instructions further cause the processor to:
calibrate the preset transformation matrix based on color data acquired from a calibration color target including a color target with known spectral characteristics.

3. The spectral characteristic acquiring apparatus according to claim 2, wherein
the object is arranged within a conveyance range of the plurality of spectral sensors; and
the color target of the calibration color target is arranged within the conveyance range of the plurality of spectral sensors, at a region other than a region where the conveyed object is arranged.

4. The spectral characteristic acquiring apparatus according to claim 3, wherein
the color target has a band-shaped configuration, and
the color target is arranged in the calibration color target so that a longitudinal direction of the color target is substantially parallel to the predetermined conveying direction.

5. The spectral characteristic acquiring apparatus according to claim 2, wherein
the calibration color target includes a white color target, a black color target, and a plurality of the color targets in different colors.

6. The spectral characteristic acquiring apparatus according to claim 1, wherein the program instructions further cause the processor to:
switch operation modes between a calibration mode for acquiring color data of a calibration color target and a spectral characteristic acquisition mode for acquiring the color data of the conveyed object.

7. An image forming apparatus configured to change an image forming condition based on spectral characteristics of a recording medium surface, the image forming apparatus comprising:
the spectral characteristic acquiring apparatus according to claim 1.

8. An image forming system comprising:
an image forming apparatus configured to change an image forming condition based on spectral characteristics of a recording medium surface; and
the spectral characteristic acquiring apparatus according to claim 1.

9. An image forming apparatus management system comprising:
an image forming apparatus configured to form a predetermined pattern on a recording medium;
the spectral characteristic acquiring apparatus according to claim 1 that is configured to acquire spectral characteristics of the predetermined pattern formed by the image forming apparatus; and
a storage apparatus configured to store identification information for identifying the image forming apparatus and the acquired spectral characteristics of the predetermined pattern in association with each other.

10. An image forming apparatus management method using the spectral characteristic acquiring apparatus according to claim 1, the image forming apparatus management method comprising:
a pattern forming step of having an image forming apparatus form a predetermined pattern on a recording medium;
a spectral characteristic acquisition step of having the spectral characteristic acquiring apparatus acquire spectral characteristics of the predetermined pattern formed by the image forming apparatus; and
a storage step of storing identification information for identifying the image forming apparatus and the acquired spectral characteristics of the predetermined pattern in association with each other.

* * * * *